(12) United States Patent
Watanabe et al.

(10) Patent No.: US 7,803,578 B2
(45) Date of Patent: Sep. 28, 2010

(54) HEAT-RESISTANT NITRILE HYDRATASE

(75) Inventors: Fumiaki Watanabe, Yokohama (JP); Dai Ujihara, Ashigarakami-gun (JP); Miki Sakai, Tokyo (JP); Fujio Yu, Yokohama (JP); Tetsuji Nakamura, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 176 days.

(21) Appl. No.: 11/947,955

(22) Filed: Nov. 30, 2007

(65) Prior Publication Data

US 2009/0162894 A1   Jun. 25, 2009

Related U.S. Application Data

(62) Division of application No. 11/569,529, filed as application No. PCT/JP2005/010107 on May 26, 2005, now Pat. No. 7,645,605.

(30) Foreign Application Priority Data

May 26, 2004  (JP)  .............................. 2004-156593
Aug. 18, 2004  (JP)  .............................. 2004-237888

(51) Int. Cl.
C12P 21/06 (2006.01)
C12N 9/00 (2006.01)
C12N 9/88 (2006.01)
C12N 1/20 (2006.01)
C12N 15/00 (2006.01)
C07H 21/04 (2006.01)

(52) U.S. Cl. ...................... 435/69.1; 435/183; 435/232; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,731,176 | A | 3/1998 | Yamada et al. |
| 5,753,472 | A | 5/1998 | Yamada et al. |
| 2007/0009985 | A1 | 1/2007 | Yamaki et al. |

FOREIGN PATENT DOCUMENTS

| | | | |
|---|---|---|---|
| EP | 1 586 637 | | 10/2005 |
| JP | 4-211379 | A | 8/1992 |
| JP | 2004-215513 | A | 8/1994 |
| JP | 6-303971 | A | 11/1994 |
| JP | 2001 292772 | | 10/2001 |
| JP | 2004-222538 | A | 8/2004 |
| WO | WO-2004/056990 | A1 | 7/2004 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Brandao, et al. Diversity of nitrile hydratase and amidase emzyme genes in *Rhodococcus erythropolis* recovered from geographically distinct habitats, Applied and Environmental Microbiology, vol. 69, No. 10, Oct. 2003, pp. 5754-5766, XP002434495.
Kato, et al. Nitrile Hydratase Involved in Aldoxime Metabolism From *Rhodococcus* Sp. Strain YH3-3 Purification and Characterization, European Journal of Biochemistry, vol. 263, pp. 662-670, 1999, XP001063100.
"Developments in Directed Evolution for Improving Enzyme Functions" by Sen et al., Appl Biochem Biotechnol, Dec. 2007, 143(3), pp. 212-223.
Chica et al. Curr Opin Biotechnol. Aug. 16, 2005 (4), pp. 378-384.
International Search Report for PCT/JP2005/010107 mailed Aug. 30, 2005.
"Cloning, nucleotide sequence and expression in *Escherichia coil* of two cobalt-containing nitrite hydratase genes from *Rhodococcus rhodochrous* J1" by Kobayashi et al., Biochimica et Biophysics Acta, vol. 1129, No. 1, Dec. 2, 1991, pp. 23-33.
"Seitai Shokubai Process: Nitrite Kagobutsu no Koso Henkan Hanno to Oyo (*Biocatalyst Process: Enzymatic Transformation of Nitrite Compounds and The Application*)", by Ryuno et al., Yuki Gosei Kagaku Kyokaishi, vol. 61, No. 5, May 1, 2003, pp. 517-521.

* cited by examiner

*Primary Examiner*—Christian L Fronda
(74) *Attorney, Agent, or Firm*—McDermott Will & Emery LLP

(57) ABSTRACT

The present invention provides: a protein having an improved nitrile hydratase activity, whereby heat resistance has been improved when compared with a wild-type nitrile hydratase activity, wherein the amino acid sequence of a nitrile hydratase is modified; a gene DNA encoding the above protein; a recombinant vector having the above gene DNA; a transformant or transductant having the above recombinant vector; a nitrile hydratase collected from a culture of the above transformant or transductant, and a production method thereof; and a method for producing an amide compound.

15 Claims, 8 Drawing Sheets

SEQUENCE LISTING

<160> NUMBER OF SEQ ID NOS: 30

<210> SEQ ID NO 1

<211> LENGTH: 690
<212> TYPE: DNA
<213> ORGANISM: Rhodococcus rhodochrous
<220> FEATURE:
<221> NAME/KEY: CDS
<222> LOCATION: (1)..(687)

<400> SEQUENCE: 1

| | | | | | | | | | | | | | | | | |
|---|---|---|---|---|---|---|---|---|---|---|---|---|---|---|---|---|
| atg | gat | ggt | atc | cac | gac | aca | ggc | ggc | atg | acc | gga | tac | gga | ccg | gtc | 48 |
| Met | Asp | Gly | Ile | His | Asp | Thr | Gly | Gly | Met | Thr | Gly | Tyr | Gly | Pro | Val | |
| 1 | | | | 5 | | | | | 10 | | | | | 15 | | |
| ccc | tat | cag | aag | gac | gag | ccc | ttc | ttc | cac | tac | gag | tgg | gag | ggt | cgg | 96 |
| Pro | Tyr | Gln | Lys | Asp | Glu | Pro | Phe | Phe | His | Tyr | Glu | Trp | Glu | Gly | Arg | |
| | | | 20 | | | | | 25 | | | | | 30 | | | |
| acc | ctg | tca | att | ctg | act | tgg | atg | cat | ctc | aag | ggc | ata | tcg | tgg | tgg | 144 |
| Thr | Leu | Ser | Ile | Leu | Thr | Trp | Met | His | Leu | Lys | Gly | Ile | Ser | Trp | Trp | |
| | | 35 | | | | | 40 | | | | | 45 | | | | |
| gac | aag | tcg | cgg | ttc | ttc | cgg | gag | tcg | atg | ggg | aac | gaa | aac | tac | gtc | 192 |
| Asp | Lys | Ser | Arg | Phe | Phe | Arg | Glu | Ser | Met | Gly | Asn | Glu | Asn | Tyr | Val | |
| | 50 | | | | | 55 | | | | | 60 | | | | | |
| aac | gag | att | cgc | aac | tcg | tac | tac | acc | cac | tgg | ctg | agt | gcg | gca | gaa | 240 |
| Asn | Glu | Ile | Arg | Asn | Ser | Tyr | Tyr | Thr | His | Trp | Leu | Ser | Ala | Ala | Glu | |
| 65 | | | | | 70 | | | | | 75 | | | | | 80 | |
| cgt | atc | ctc | gtc | gcc | gac | aag | atc | atc | acc | gaa | gaa | gag | cga | aag | cac | 288 |
| Arg | Ile | Leu | Val | Ala | Asp | Lys | Ile | Ile | Thr | Glu | Glu | Glu | Arg | Lys | His | |
| | | | | 85 | | | | | 90 | | | | | 95 | | |
| cgt | gtg | caa | gag | atc | ctt | gag | ggt | cgg | tac | acg | gac | agg | aag | ccg | tcg | 336 |
| Arg | Val | Gln | Glu | Ile | Leu | Glu | Gly | Arg | Tyr | Thr | Asp | Arg | Lys | Pro | Ser | |
| | | | 100 | | | | | 105 | | | | | 110 | | | |
| cgg | aag | ttc | gat | ccg | gcc | cag | atc | gag | aag | gcg | atc | gaa | cgg | ctt | cac | 384 |
| Arg | Lys | Phe | Asp | Pro | Ala | Gln | Ile | Glu | Lys | Ala | Ile | Glu | Arg | Leu | His | |
| | | 115 | | | | | 120 | | | | | 125 | | | | |
| gag | ccc | cac | tcc | cta | gcg | ctt | cca | gga | gcg | gag | ccg | agt | ttc | tct | ctc | 432 |
| Glu | Pro | His | Ser | Leu | Ala | Leu | Pro | Gly | Ala | Glu | Pro | Ser | Phe | Ser | Leu | |
| 130 | | | | | 135 | | | | | 140 | | | | | | |
| ggt | gac | aag | atc | aaa | gtg | aag | agt | atg | aac | ccg | ctg | gga | cac | aca | cgg | 480 |
| Gly | Asp | Lys | Ile | Lys | Val | Lys | Ser | Met | Asn | Pro | Leu | Gly | His | Thr | Arg | |
| 145 | | | | | 150 | | | | | 155 | | | | | 160 | |
| tgc | ccg | aaa | tat | gtg | cgg | aac | aag | atc | ggg | gaa | atc | gtc | gcc | tac | cac | 528 |
| Cys | Pro | Lys | Tyr | Val | Arg | Asn | Lys | Ile | Gly | Glu | Ile | Val | Ala | Tyr | His | |
| | | | | 165 | | | | | 170 | | | | | 175 | | |
| ggc | tgc | cag | atc | tat | ccc | gag | agc | agc | tcc | gcc | ggc | ctc | ggc | gac | gat | 576 |
| Gly | Cys | Gln | Ile | Tyr | Pro | Glu | Ser | Ser | Ser | Ala | Gly | Leu | Gly | Asp | Asp | |
| | | | 180 | | | | | 185 | | | | | 190 | | | |
| cct | cgc | ccg | ctc | tac | acg | gtc | gcg | ttt | tcc | gcc | cag | gaa | ctg | tgg | ggc | 624 |
| Pro | Arg | Pro | Leu | Tyr | Thr | Val | Ala | Phe | Ser | Ala | Gln | Glu | Leu | Trp | Gly | |
| | | 195 | | | | | 200 | | | | | 205 | | | | |
| gac | gac | gga | aac | ggg | aaa | gac | gta | gtg | tgc | gtc | gat | ctc | tgg | gaa | ccg | 672 |
| Asp | Asp | Gly | Asn | Gly | Lys | Asp | Val | Val | Cys | Val | Asp | Leu | Trp | Glu | Pro | |
| 210 | | | | | 215 | | | | | 220 | | | | | | |
| tac | ctg | atc | tct | gcg | tga | | | | | | | | | | | 690 |
| Tyr | Leu | Ile | Ser | Ala | | | | | | | | | | | | |
| 225 | | | | | | | | | | | | | | | | |

<210> SEQ ID NO 2
<211> LENGTH: 229
<212> TYPE: PRT
<213> ORGANISM: Rhodococcus rhodochrous

<400> SEQUENCE: 2

| | | | | | | | | | | | | | | | |
|---|---|---|---|---|---|---|---|---|---|---|---|---|---|---|---|
| Met | Asp | Gly | Ile | His | Asp | Thr | Gly | Gly | Met | Thr | Gly | Tyr | Gly | Pro | Val |
| 1 | | | | 5 | | | | | 10 | | | | | 15 | |

```
Pro Tyr Gln Lys Asp Glu Pro Phe Phe His Tyr Glu Trp Glu Gly Arg
            20                  25                  30

Thr Leu Ser Ile Leu Thr Trp Met His Leu Lys Gly Ile Ser Trp Trp
            35                  40                  45

Asp Lys Ser Arg Phe Phe Arg Glu Ser Met Gly Asn Glu Asn Tyr Val
        50                  55                  60

Asn Glu Ile Arg Asn Ser Tyr Tyr Thr His Trp Leu Ser Ala Ala Glu
65                  70                  75                  80

Arg Ile Leu Val Ala Asp Lys Ile Ile Thr Glu Glu Arg Lys His
                85                  90                  95

Arg Val Gln Glu Ile Leu Glu Gly Arg Tyr Thr Asp Arg Lys Pro Ser
            100                 105                 110

Arg Lys Phe Asp Pro Ala Gln Ile Glu Lys Ala Ile Glu Arg Leu His
        115                 120                 125

Glu Pro His Ser Leu Ala Leu Pro Gly Ala Glu Pro Ser Phe Ser Leu
    130                 135                 140

Gly Asp Lys Ile Lys Val Lys Ser Met Asn Pro Leu Gly His Thr Arg
145                 150                 155                 160

Cys Pro Lys Tyr Val Arg Asn Lys Ile Gly Glu Ile Val Ala Tyr His
                165                 170                 175

Gly Cys Gln Ile Tyr Pro Glu Ser Ser Ala Gly Leu Gly Asp Asp
            180                 185                 190

Pro Arg Pro Leu Tyr Thr Val Ala Phe Ser Ala Gln Glu Leu Trp Gly
        195                 200                 205

Asp Asp Gly Asn Gly Lys Asp Val Val Cys Val Asp Leu Trp Glu Pro
    210                 215                 220

Tyr Leu Ile Ser Ala
225

<210> SEQ ID NO 3
<211> LENGTH: 612
<212> TYPE: DNA
<213> ORGANISM: Rhodococcus rhodochrous
<220> FEATURE:
<221> NAME/KEY: CDS
<222> LOCATION: (1)..(609)

<400> SEQUENCE: 3 gtg agc gag cac gtc aat aag tac acg gag tac gag gca cgt acc aag      48
Met Ser Glu His Val Asn Lys Tyr Thr Glu Tyr Glu Ala Arg Thr Lys
1               5                   10                  15 gcg atc gaa acc ttg ctg tac gag cga ggg ctc atc acg ccc gcc gcg      96
Ala Ile Glu Thr Leu Leu Tyr Glu Arg Gly Leu Ile Thr Pro Ala Ala
            20                  25                  30 gtc gac cga gtc gtt tcg tac tac gag aac gag atc ggc ccg atg ggc     144
Val Asp Arg Val Val Ser Tyr Tyr Glu Asn Glu Ile Gly Pro Met Gly
        35                  40                  45 ggt gcc aag gtc gtg gcc aag tcc tgg gtg gac cct gag tac cgc aag     192
Gly Ala Lys Val Val Ala Lys Ser Trp Val Asp Pro Glu Tyr Arg Lys
    50                  55                  60 tgg ctc gaa gag gac gcg acg gcc gcg atg gcg tca ttg ggc tat gcc     240
Trp Leu Glu Glu Asp Ala Thr Ala Ala Met Ala Ser Leu Gly Tyr Ala
65                  70                  75                  80 ggt gag cag gca cac caa att tcg gcg gtc ttc aac gac tcc caa acg     288
Gly Glu Gln Ala His Gln Ile Ser Ala Val Phe Asn Asp Ser Gln Thr
                85                  90                  95 cat cac gtg gtg gtg tgc act ctg tgt tcg tgc tat ccg tgg ccg gtg     336
```

```
His His Val Val Val Cys Thr Leu Cys Ser Cys Tyr Pro Trp Pro Val
            100                 105                 110 ctt ggt ctc ccg ccc gcc tgg tac aag agc atg gag tac cgg tcc cga      384
Leu Gly Leu Pro Pro Ala Trp Tyr Lys Ser Met Glu Tyr Arg Ser Arg
        115                 120                 125 gtg gta gcg gac cct cgt gga gtc ctc aag cgc gat ttc ggt ttc gac      432
Val Val Ala Asp Pro Arg Gly Val Leu Lys Arg Asp Phe Gly Phe Asp
    130                 135                 140 atc ccc gat gag gtg gag gtc agg gtt tgg gac agc agc tcc gaa atc      480
Ile Pro Asp Glu Val Glu Val Arg Val Trp Asp Ser Ser Ser Glu Ile
145                 150                 155                 160 cgc tac atc gtc atc ccg gaa cgg ccg gcc ggc acc gac ggt tgg tcc      528
Arg Tyr Ile Val Ile Pro Glu Arg Pro Ala Gly Thr Asp Gly Trp Ser
                165                 170                 175 gag gag gag ctg acg aag ctg gtg agc cgg gac tcg atg atc ggt gtc      576
Glu Glu Glu Leu Thr Lys Leu Val Ser Arg Asp Ser Met Ile Gly Val
            180                 185                 190 agt aat gcg ctc aca ccg cag gaa gtg atc gta tga                       612
Ser Asn Ala Leu Thr Pro Gln Glu Val Ile Val
        195                 200
```

<210> SEQ ID NO 4
<211> LENGTH: 203
<212> TYPE: PRT
<213> ORGANISM: Rhodococcus rhodochrous

<400> SEQUENCE: 4

```
Met Ser Glu His Val Asn Lys Tyr Thr Glu Tyr Glu Ala Arg Thr Lys
1               5                   10                  15

Ala Ile Glu Thr Leu Leu Tyr Glu Arg Gly Leu Ile Thr Pro Ala Ala
            20                  25                  30

Val Asp Arg Val Val Ser Tyr Tyr Glu Asn Glu Ile Gly Pro Met Gly
        35                  40                  45

Gly Ala Lys Val Val Ala Lys Ser Trp Val Asp Pro Glu Tyr Arg Lys
    50                  55                  60

Trp Leu Glu Glu Asp Ala Thr Ala Ala Met Ala Ser Leu Gly Tyr Ala
65                  70                  75                  80

Gly Glu Gln Ala His Gln Ile Ser Ala Val Phe Asn Asp Ser Gln Thr
                85                  90                  95

His His Val Val Val Cys Thr Leu Cys Ser Cys Tyr Pro Trp Pro Val
            100                 105                 110

Leu Gly Leu Pro Pro Ala Trp Tyr Lys Ser Met Glu Tyr Arg Ser Arg
        115                 120                 125

Val Val Ala Asp Pro Arg Gly Val Leu Lys Arg Asp Phe Gly Phe Asp
    130                 135                 140

Ile Pro Asp Glu Val Glu Val Arg Val Trp Asp Ser Ser Ser Glu Ile
145                 150                 155                 160

Arg Tyr Ile Val Ile Pro Glu Arg Pro Ala Gly Thr Asp Gly Trp Ser
                165                 170                 175

Glu Glu Glu Leu Thr Lys Leu Val Ser Arg Asp Ser Met Ile Gly Val
            180                 185                 190

Ser Asn Ala Leu Thr Pro Gln Glu Val Ile Val
        195                 200
```

<210> SEQ ID NO 5
<211> LENGTH: 24
<212> TYPE: DNA
<213> ORGANISM: Artificial sequence

```
<220> FEATURE:
<223> OTHER INFORMATION: Synthetic DNA

<400> SEQUENCE: 5
ggaatgaggc catggatggt atcc                                              24

<210> SEQ ID NO 6
<211> LENGTH: 31
<212> TYPE: DNA
<213> ORGANISM: Artificial sequence
<220> FEATURE:
<223> OTHER INFORMATION: Synthetic DNA

<400> SEQUENCE: 6
gcgtaagctt ccgcgagatc agtatccacc g                                      31

<210> SEQ ID NO 7
<211> LENGTH: 30
<212> TYPE: DNA
<213> ORGANISM: Artificial sequence
<220> FEATURE:
<223> OTHER INFORMATION: Synthetic DNA

<400> SEQUENCE: 7
ggaattcgta taatgtgtgg aattgtgagc                                        30

<210> SEQ ID NO 8
<211> LENGTH: 25
<212> TYPE: DNA
<213> ORGANISM: Artificial sequence
<220> FEATURE:
<223> OTHER INFORMATION: Synthetic DNA

<400> SEQUENCE: 8
ggctgaaaat cttctctcat ccgcc                                             25

<210> SEQ ID NO 9
<211> LENGTH: 35
<212> TYPE: DNA
<213> ORGANISM: Artificial sequence
<220> FEATURE:
<223> OTHER INFORMATION: Synthetic DNA

<400> SEQUENCE: 9
gatcatcacc gaagaagggc gaaagcaccg tgtgc                                  35

<210> SEQ ID NO 10
<211> LENGTH: 35
<212> TYPE: DNA
<213> ORGANISM: Artificial sequence
<220> FEATURE:
<223> OTHER INFORMATION: Synthetic DNA

<400> SEQUENCE: 10
gcacacggtg ctttcgccct tcttcggtga tgatc                                  35

<210> SEQ ID NO 11
<211> LENGTH: 41
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (20)..(21)
<223> OTHER INFORMATION: n is a, c, g, or t
```

```
<400> SEQUENCE: 11
caagatcatc accgaagaan nscgaaagca ccgtgtgcaa g                           41

<210> SEQ ID NO 12
<211> LENGTH: 41
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (21)..(22)
<223> OTHER INFORMATION: n is a, c, g, or t

<400> SEQUENCE: 12
cttgcacacg gtgctttcgs nnttcttcgg tgatgatctt g                           41

<210> SEQ ID NO 13
<211> LENGTH: 41
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (20)..(21)
<223> OTHER INFORMATION: n is a, c, g, or t

<400> SEQUENCE: 13
gtgcccgaaa tatgtgcggn nsaagatcgg ggaaatcgtc g                           41

<210> SEQ ID NO 14
<211> LENGTH: 41
<212> TYPE: DNA
<213> ORGANISM: Artificial sequence
<220> FEATURE:
<223> OTHER INFORMATION: Synthetic DNA
<220> FEATURE:
<221> NAME/KEY: misc_feature
<222> LOCATION: (21)..(22)
<223> OTHER INFORMATION: n is a, c, g, or t

<400> SEQUENCE: 14
cgacgatttc cccgatctts nnccgcacat atttcgggca c                           41

<210> SEQ ID NO 15
<211> LENGTH: 35
<212> TYPE: DNA
<213> ORGANISM: Artificial sequence
<220> FEATURE:
<223> OTHER INFORMATION: Synthetic DNA

<400> SEQUENCE: 15
ccatggatgg tatccacgac acaggcggca tgacc                                  35

<210> SEQ ID NO 16
<211> LENGTH: 34
<212> TYPE: DNA
<213> ORGANISM: Artificial sequence
<220> FEATURE:
<223> OTHER INFORMATION: Synthetic DNA

<400> SEQUENCE: 16
aagcttcacg ctggcctcga gcgcctttgt ccag                                   34

<210> SEQ ID NO 17
<211> LENGTH: 1565
```

<212> TYPE: DNA
<213> ORGANISM: Rhodococcus rhodochrous

<400> SEQUENCE: 17

```
ccatggatgg tatccacgac acaggcggca tgaccggata cggaccggtc ccctatcaga      60
aggacgagcc cttcttccac tacgagtggg agggtcggac cctgtcgatt ctgacctgga     120
tgcatctcaa gggcatgtcg tggtgggaca agtcgcggtt cttccgggag tcgatgggga     180
acgaaaacta cgtcaacgag attcgcaact cgtactacac ccactggctg agtgcggcag     240
aacgtatcct cgtcgccgac aagatcatca ccgaagaaga gcgaaagcac cgtgtgcagg     300
agatcctcga gggtcggtac acggacagga acccgtcgcg gaagttcgat ccggccgaga     360
tcgagaaggc gatcgaacgg cttcacgagc cccactccct agcacttcca ggagcggagc     420
cgagtttctc cctcggtgac aaggtcaaag tgaagaatat gaacccgctg gacacacac      480
ggtgcccgaa atatgtgcgg aacaagatcg gggaaatcgt cacctcccac ggctgccaga     540
tctatcccga gagcagctcc gccggcctcg gcgacgatcc ccgcccgctc tacacggtcg     600
cgttttccgc ccaggaactg tggggcgacg acggaaacgg gaaagacgta gtgtgcgtcg     660
atctctggga accgtacctg atctctgcgt gaaaggaata cgatagtgag cgagcacgtc     720
aataagtaca cggagtacga ggcacgtacc aaggcaatcg aaactttgct gtacgagcga     780
gggctcatca cgcccgccgc ggtcgaccga gtcgtttcgt actacgagaa cgagatcggc     840
ccgatgggcg gtgccaaggt cgtggcgaag tcctgggtgg accctgagta ccgcaagtgg     900
ctcgaagagg acgcgacggc cgcgatggcg tcattgggct atgccggtga gcaggcacac     960
caaatttcgg cggtcttcaa cgactcccaa acgcatcacg tggtggtgtg cactctgtgt    1020
tcgtgctatc cgtggccggt gcttggtctc ccgcccgcct ggtacaagag catggagtac    1080
cggtcccgag tggtagcgga ccctcgtgga gtgctcaagc gcgatttcgg tttcgacatc    1140
cccgatgagg tggaggtcag ggtttgggac agcagctccg aaatccgcta catcgtcatc    1200
ccggaacggc cggccggcac cgacggttgg tccgaggacg agctggcgaa gctggtgagt    1260
cgggactcga tgatcggtgt cagtaatgcg ctcacacccc aggaagtgat cgtatgagtg    1320
aagacacact cactgatcgg ctcccggcga ctgggaccgc cgcaccgccc cgcgacaatg    1380
gcgagcttgt attcaccgag ccttgggaag caacggcatt cggggtcgcc atcgcgcttt    1440
cggatcagaa gtcgtacgaa tgggagttct tccgacagcg tctcattcac tccatcgctg    1500
aggccaacgg ttgcgaggca tactacgaga gctggacaaa ggcgctcgag gccagcgtga    1560
agctt                                                              1565
```

<210> SEQ ID NO 18
<211> LENGTH: 35
<212> TYPE: DNA
<213> ORGANISM: Artificial sequence
<220> FEATURE:
<223> OTHER INFORMATION: Synthetic DNA

<400> SEQUENCE: 18

```
cccgaaatat gtgcggagca agatcgggga aatcg                                35
```

<210> SEQ ID NO 19
<211> LENGTH: 35
<212> TYPE: DNA
<213> ORGANISM: Artificial sequence
<220> FEATURE:
<223> OTHER INFORMATION: Synthetic DNA

```
<400> SEQUENCE: 19
cgatttcccc gatcttgctc cgcacatatt tcggg                              35

<210> SEQ ID NO 20
<211> LENGTH: 31
<212> TYPE: DNA
<213> ORGANISM: Artificial sequence
<220> FEATURE:
<223> OTHER INFORMATION: Synthetic DNA

<400> SEQUENCE: 20
ggagccgagt ttctctcacg gtgacaagat c                                 31

<210> SEQ ID NO 21
<211> LENGTH: 31
<212> TYPE: DNA
<213> ORGANISM: Artificial sequence
<220> FEATURE:
<223> OTHER INFORMATION: Synthetic DNA

<400> SEQUENCE: 21
gatcttgtca ccgtgagaga aactcggctc c                                 31

<210> SEQ ID NO 22
<211> LENGTH: 33
<212> TYPE: DNA
<213> ORGANISM: Artificial sequence
<220> FEATURE:
<223> OTHER INFORMATION: Synthetic DNA

<400> SEQUENCE: 22
gaaagacgta gtgtgcgccg atctctggga acc                               33

<210> SEQ ID NO 23
<211> LENGTH: 33
<212> TYPE: DNA
<213> ORGANISM: Artificial sequence
<220> FEATURE:
<223> OTHER INFORMATION: Synthetic DNA

<400> SEQUENCE: 23
ggttcccaga gatcggcgca cactacgtct ttc                               33

<210> SEQ ID NO 24
<211> LENGTH: 32
<212> TYPE: DNA
<213> ORGANISM: Artificial sequence
<220> FEATURE:
<223> OTHER INFORMATION: Synthetic DNA

<400> SEQUENCE: 24
gagtaccggt cccgagcggt agcggaccct cg                                32

<210> SEQ ID NO 25
<211> LENGTH: 32
<212> TYPE: DNA
<213> ORGANISM: Artificial sequence
<220> FEATURE:
<223> OTHER INFORMATION: Synthetic DNA

<400> SEQUENCE: 25
cgagggtccg ctaccgctcg ggaccggtac tc                                32

<210> SEQ ID NO 26
<211> LENGTH: 20
```

-continued

```
<212> TYPE: DNA
<213> ORGANISM: Artificial sequence
<220> FEATURE:
<223> OTHER INFORMATION: Synthetic DNA

<400> SEQUENCE: 26
aacgtcgaca ccggtggtgg                                              20

<210> SEQ ID NO 27
<211> LENGTH: 28
<212> TYPE: DNA
<213> ORGANISM: Artificial sequence
<220> FEATURE:
<223> OTHER INFORMATION: Synthetic DNA

<400> SEQUENCE: 27
ccgcgacttg tcccgccacg atatgccc                                     28

<210> SEQ ID NO 28
<211> LENGTH: 20
<212> TYPE: DNA
<213> ORGANISM: Artificial sequence
<220> FEATURE:
<223> OTHER INFORMATION: Synthetic DNA

<400> SEQUENCE: 28
gtacccgggg atccactaga                                              20

<210> SEQ ID NO 29
<211> LENGTH: 20
<212> TYPE: DNA
<213> ORGANISM: Artificial sequence
<220> FEATURE:
<223> OTHER INFORMATION: Synthetic DNA

<400> SEQUENCE: 29
ccttagtcag cttctgtccg                                              20

<210> SEQ ID NO 30
<211> LENGTH: 30
<212> TYPE: DNA
<213> ORGANISM: Artificial sequence
<220> FEATURE:
<223> OTHER INFORMATION: Synthetic DNA

<400> SEQUENCE: 30
ccctcccact cgtagcggaa gaagggctcg                                   30
```

HEAT-RESISTANT NITRILE HYDRATASE

CROSS-REFERENCE TO PRIOR APPLICATION

This is a divisional application of U.S. application Serial No. 11/569,529, filed Nov. 22, 2006 which claims the benefit of priority of a U.S. National Phase Application under 35 U.S.C. §371 of International Patent Application No. PCT/JP2005/010107 filed May 26, 2005, and claims the benefit of Japanese Patent Application Nos. 2004-156593 filed May 26, 2004 and 2004-237888 filed Aug. 18, 2004 all of them are incorporated by reference herein. The International Application was published in Japanese on Dec. 8, 2005 as WO 2005/116205 A1 under PCT article 21(2).

TECHNICAL FIELD

The present invention relates to: a protein having an improved nitrile hydratase activity, whereby heat resistance has been improved or substrate specificity has been changed; a gene DNA encoding the above protein; a recombinant vector comprising the above gene DNA; a transformant or transductant having the above recombinant vector; a nitrile hydratase collected from a culture of the above transformant or transductant, and a production method thereof; and a method for producing an amide compound using the above culture or a treated product thereof.

BACKGROUND ART

In recent years, a nitrile hydratase, which is an enzyme having an activity of hydrating a nitrile group and converting it to an amide group, has been discovered. A method for producing from a nitrile compound, an amide compound corresponding thereto, using the above enzyme, the cell mass of microorganisms containing the above enzyme, or the like, has been disclosed. This production method has been known as a method, which brings on a higher conversion rate to convert a nitrile compound to an amide compound corresponding thereto and a higher selectivity than those of the conventional chemical synthesis method.

Examples of the microorganisms that produce a nitrile hydratase may include microorganisms belonging to genus *Corynebacterium*, genus *Pseudomonas*, genus *Rhodococcus*, genus *Rhizobium*, genus *Klebsiella*, genus *Pseudonocardia*, or the like. Of these, *Rhodococcus rhodochrous* J-1 strain has been used for the industrial production of acrylamide, and the usefulness thereof has been verified. In addition, a gene encoding a nitrile hydratase generated from the cell strain has also been discovered (refer to Reference 1). Moreover, from the viewpoint of reduction in the amount of enzyme used during the reaction and cost reduction, it has been desired that an enzyme having an improved heat resistance be obtained.

A nitrile hydratase isolated from microorganisms existing in nature or the gene thereof has been used. On the other hand, an attempt to introduce a mutation into a nitrile hydratase has been made for the purpose of altering the nitrile hydratase in terms of its activity, substrate specificity, Vmax, Km, heat stability, stability to substrate, stability to the product generated, etc. (refer to References 2 and 3).

REFERENCES

1: Japanese Patent No. 3162091
2: International Publication WO2004/056990
3: Japanese Patent Application Laid-Open No. 2004-222538

DISCLOSURE OF THE INVENTION

Nitrile hydratase is an enzyme that has already been used for the industrial production of acrylamide. The obtainment of an enzyme having properties such as heat resistance, which are more improved than those of the currently used enzyme, is considered to be useful in terms of cost reduction during the enzyme reaction.

Thus, it is an object of the present invention to provide: a protein having an improved nitrile hydratase activity, whereby heat resistance has been improved, which is obtained by further improving a nitrile hydratase; a gene DNA encoding the above protein; a recombinant vector having the above gene DNA; a transformant or transductant having the above recombinant vector; a nitrile hydratase collected from the culture of the above transformant or transductant, and a production method thereof; and a method for producing an amide compound using the above culture or the treated product thereof.

The nitrile hydratase from the *Rhodococcus rhodochrous* J-1 strain has been used for the industrial production of acrylamide using acrylonitrile as a raw material. However, this nitrile hydratase has a low reactivity to aromatic nitrile. Hence, an enzyme having a high reactivity to aromatic nitrile has been desired. At the same time, from the viewpoint of cost reduction regarding catalysts, an enzyme that is stable to heat and is hardly deactivated has been required. Thus, it is an object of the present invention is to improve a nitrile hydratase to obtain an enzyme having an improved heat resistance and/or to obtain an enzyme having an improved reactivity to aromatic nitrile.

As a result of intensive studies to solve the aforementioned problems, the present inventor has found that the heat resistance of a nitrile hydratase derived from the *Rhodococcus rhodochrous* J-1 strain is improved and/or that the reactivity of the enzyme to aromatic nitrile is improved by substituting at least one or more amino acid residue in the amino acid sequence of the above enzyme with a residue selected from a group of natural amino acids, thereby completing the present invention. That is to say, the present invention is as follows:

(1) A protein described in the following (a), (b), or (c):

(a) a protein, which comprises an amino acid sequence wherein at least one amino acid residue selected from among the phenylalanine residue at position 24, the isoleucine residue at position 88, the glutamic acid residue at position 92, the glutamic acid residue at position 93, the histidine residue at position 96, the glutamic acid residue at position 103, the asparagine residue at position 167, and the tyrosine residue at position 225, is substituted with another amino acid residue in the amino acid sequence of the β subunit of a wild-type nitrile hydratase, and which has a heat-resistant nitrile hydratase activity;

(b) a protein, which comprises an amino acid sequence wherein the arginine residue at position 167 is substituted with another amino acid sequence in the amino acid sequence of the β subunit of a wild-type nitrile hydratase, and which has a heat-resistant nitrile hydratase activity; or (c) a protein, which comprises an amino acid sequence comprising a deletion, substitution, or addition of one or several amino acid residues in the amino acid sequence of the protein described in (a) or (b) above, and which has a heat-resistant nitrile hydratase activity.

(2) A protein described in the following (a) or (b):

(a) a protein, which comprises an amino acid sequence wherein at least one amino acid residue selected from among the asparagine residue at position 42, the alanine residue at position 80, the alanine residue at position 118, and the aspartic acid residue at position 132, is substituted with another amino acid residue in the amino acid sequence of the α subunit of a wild-type nitrile hydratase, and which has a heat-resistant nitrile hydratase activity; or (b) a protein, which comprises an amino acid sequence comprising a deletion, substitution, or addition of one or several amino acid residues in the amino acid sequence of the protein described in (a) above, and which has a heat-resistant nitrile hydratase activity.

(3) A protein described in the following (a), (b), or (c):

(a) a protein, which comprises an amino acid sequence wherein the leucine residue at position 144 or the valine residue at position 219 is substituted with another amino acid residue, in an amino acid sequence wherein the arginine residue at position 167 is substituted with another amino acid residue in the amino acid sequence of the β subunit of a wild-type nitrile hydratase, and which has a heat-resistant nitrile hydratase activity;

(b) a protein, which comprises an amino acid sequence wherein the arginine residue at position 167 is substituted with another amino acid sequence in the amino acid sequence of the β subunit of a wild-type nitrile hydratase and an amino acid sequence wherein the valine residue at position 129 or the leucine residue at position 196 is substituted with another amino acid residue in the amino acid sequence of the β subunit of a wild-type nitrile hydratase, and which has a heat-resistant nitrile hydratase activity; or (c) a protein, which comprises an amino acid sequence comprising a deletion, substitution, or addition of one or several amino acid residues in the amino acid sequence of the protein described in (a) or (b) above, and which has a heat-resistant nitrile hydratase activity.

(4) A protein described in the following (a) or (b):

(a) a protein, which comprises an amino acid sequence wherein at least one amino acid residue selected from the histidine residue at position 26 and the tryptophan residue at position 48 is substituted with another amino acid residue in the amino acid sequence of the β subunit of a wild-type nitrile hydratase, and which has a heat-resistant nitrile hydratase activity; or (b) a protein, which comprises an amino acid sequence comprising a deletion, substitution, or addition of one or several amino acid residues in the amino acid sequence of the protein described in (a) above, and which has a heat-resistant nitrile hydratase activity.

(5) The protein according to (4) above, wherein the histidine residue at position 26 has been substituted with an arginine residue.

(6) The protein according to (4) above, wherein the tryptophan residue at position 48 has been substituted with any amino acid residue selected from among arginine, valine, and leucine.

(7) A gene DNA, which encodes the protein according to any one of (1) to (6) above.

(8) A gene DNA described in the following (a), (b), or (c):

(a) a gene DNA, which comprises a nucleotide sequence wherein at least one nucleotide selected from among the nucleotides at positions 70 to 72, 262 to 264, 274 to 276, 277 to 279, 286 to 288, 307 to 309, 499 to 501, and 673 to 675, is substituted with another different nucleotide in the nucleotide sequence of a gene encoding the β subunit of a wild-type nitrile hydratase, and which encodes a protein having a heat-resistant nitrile hydratase activity;

(b) a gene DNA, which comprises a nucleotide sequence wherein at least one nucleotide selected from among the nucleotides at positions 499 to 501 is substituted with another different nucleotide in the nucleotide sequence of a gene encoding the β subunit of a wild-type nitrile hydratase, and which encodes a protein having a heat-resistant nitrile hydratase activity; or (c) a gene DNA, which hybridizes with a nucleotide sequence complementary to the nucleotide sequence of the gene DNA described in (a) or (b) above under stringent conditions, and which encodes a protein having a heat-resistant nitrile hydratase activity.

(9) A gene DNA described in the following (a) or (b):

(a) a gene DNA, which comprises a nucleotide sequence wherein at least one nucleotide selected from among the nucleotides at positions 124 to 126, 238 to 240, 352 to 354, and 394 to 396, is substituted with another different nucleotide in the nucleotide sequence of a gene encoding the α subunit of a wild-type nitrile hydratase, and which encodes a protein having a heat-resistant nitrile hydratase activity; or (b) a gene DNA, which hybridizes with a nucleotide sequence complementary to the nucleotide sequence of the gene DNA described in (a) above under stringent conditions, and which encodes a protein having a heat-resistant nitrile hydratase activity.

(10) A gene DNA described in the following (a), (b), or (c):

(a) a gene DNA, which comprises a nucleotide sequence wherein at least one nucleotide selected from among the nucleotides at positions 430 to 432 and 655 to 657 is substituted with another different nucleotide in a nucleotide sequence wherein at least one nucleotide selected from among the nucleotides at positions 499 to 501 is substituted with another different nucleotide in the nucleotide sequence of a gene encoding the β subunit of a wild-type nitrile hydratase, and which encodes a protein having a heat-resistant nitrile hydratase activity;

(b) a gene DNA, which comprises a nucleotide sequence obtained wherein with another different nucleotide at least one nucleotide selected from among the nucleotides at positions 499 to 501 in the nucleotide sequence of a gene encoding the β subunit of a wild-type nitrile hydratase and the nucleotides at positions 385 to 387 and 586 to 588 in the nucleotide sequence of a gene encoding the α subunit of a wild-type nitrile hydratase is substituted, and which encodes a protein having a heat-resistant nitrile hydratase activity; or (c) a gene DNA, which hybridizes with a nucleotide sequence complementary to the nucleotide sequence of the gene DNA described in (a) or (b) above under stringent conditions, and which encodes a protein having a heat-resistant nitrile hydratase activity.

(11) A gene DNA described in the following (a) or (b):

(a) a gene DNA, which comprises a nucleotide sequence wherein at least one nucleotide selected from among the nucleotides at positions 76 to 78 and 142 to 144 is substituted with another different nucleotide in the nucleotide sequence of a gene encoding the β subunit of a wild-type nitrile hydratase, and which encodes a protein having a heat-resistant nitrile hydratase activity; or (b) a gene DNA, which hybridizes with a nucleotide sequence complementary to the nucleotide sequence of the gene DNA described in (a) above under stringent conditions, and which encodes a protein having a heat-resistant nitrile hydratase activity.

(12) The gene DNA according to (11) above, wherein base A at position 77 has been substituted with G.

(13) The gene DNA according to (11) above, wherein base T at position 142 has been substituted with C.

(14) A recombinant vector, which comprises the gene DNA according to any one of (7) to (13) above.

(15) A transformant or transductant, which comprises the recombinant vector according to (14) above.

(16) A nitrile hydratase, which is collected from a culture obtained by culturing the transformant or transductant according to (15) above.

(17) A method for producing a nitrile hydratase, which comprises culturing the transformant or transductant according to (15) above and collecting a nitrile hydratase from a obtained culture.

(18) A method for producing an amide compound, which comprises: allowing a culture obtained by culturing the transformant according to (15) above or a treated product thereof to come into contact with a nitrile compound; and collecting an amide compound generated as a result of such contact.

The present invention provides a mutant nitrile hydratase having heat resistance and/or reactivity to aromatic nitrile, which are more improved than those of a wild-type nitrile hydratase, and a gene encoding the above enzyme. In addition, the present invention also provides recombinant DNA comprising the aforementioned mutant nitrile hydratase gene, a transformant (or transductant) comprising the above recombinant DNA, and a method for producing an amide compound using the above transformant (or transductant).

The present invention enables efficient production of acrylamide.

BEST MODE FOR CARRYING OUT THE INVENTION

Figure 1:
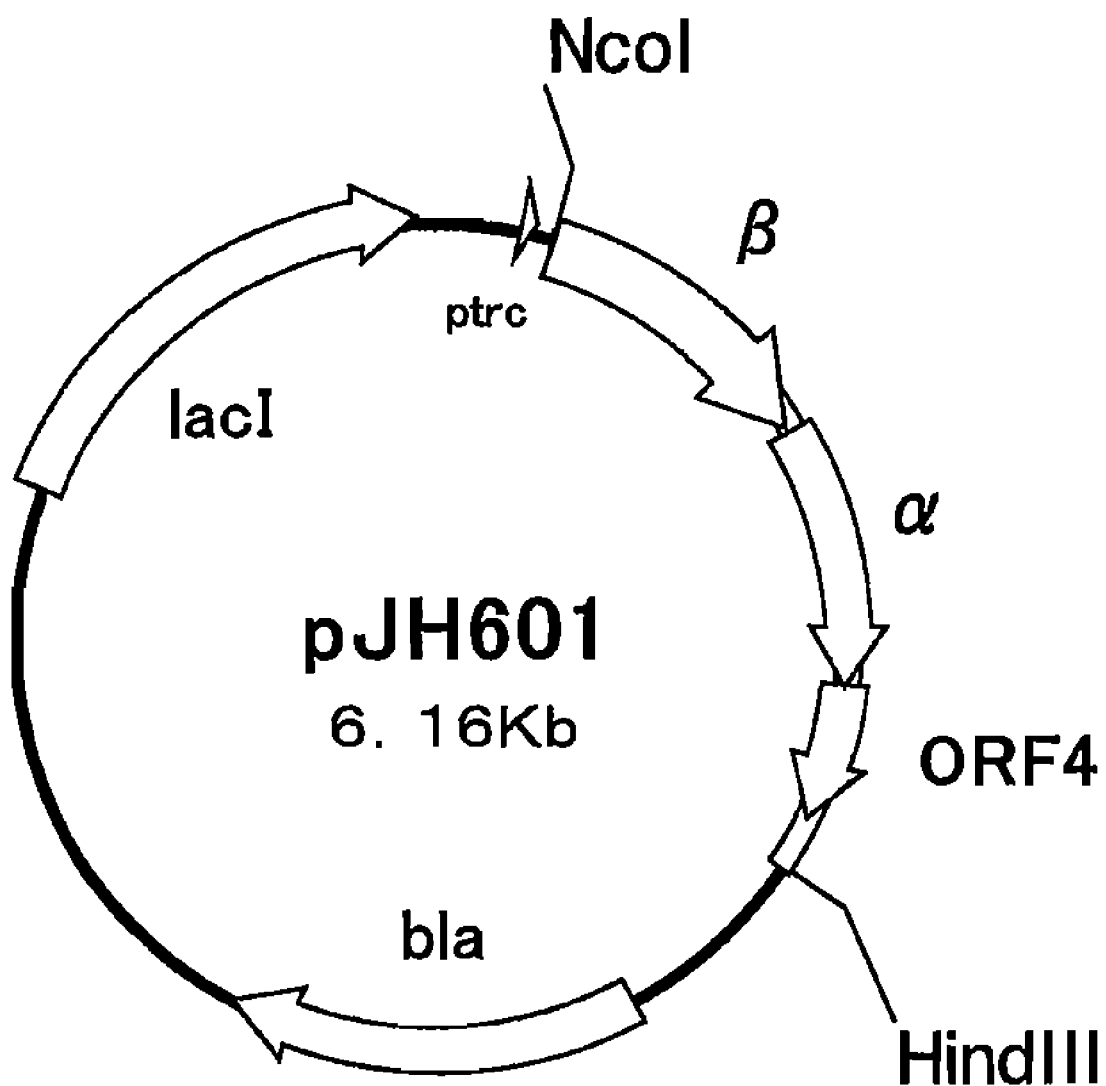
FIG. 1 is a structural view of the plasmid pJH601.

The present invention will be described in detail below. All references and patent publications such as unexamined patent publications or international publications cited herein are incorporated herein by reference.

<Nitrile Hydratase>

By mutating a portion of the amino acid sequence of a wild-type nitrile hydratase, the present invention provides an improved nitrile hydratase having a heat resistance and/or a substrate specificity that are more improved than those of a wild-type nitrile hydratase.

The term "nitrile hydratase" is used herein to mean an enzyme catalyzing a hydration reaction to convert a nitrile compound to an amide compound corresponding thereto ($RCN+H_2O \rightarrow RCONH_2$). In addition, such "nitrile hydratase" adopts a higher order structure whereby α subunits and β subunits aggregate. The term "wild-type nitrile hydratase" is used herein to mean a nitrile hydratase having an amino acid sequence derived from a wild-type strain (parent strain) of a microorganism acting as an enzyme source thereof, or a nitrile hydratase encoded by a gene sequence derived from such a wild-type strain (parent strain). The term "wild-type β subunit" or "wild-type α subunit" is used herein to mean a β subunit or α subunit having an amino acid sequence derived from a wild-type strain (parent strain), or a β subunit or α subunit encoded by a gene sequence derived from such a wild-type strain (parent strain).

Examples of such a "wild-type nitrile hydratase" may include nitrile hydratases derived from various types of wild-type microorganisms. The types of such microorganisms are not particularly limited, as long as they are microorganisms having a gene encoding a nitrile hydratase. Preferred examples of such a nitrile hydratase may include nitrile hydratases having amino acid sequences derived from microorganisms belonging to genus Rhodococcus, such as Rhodococcus rhodochrous J-1 (FERM BP-1478), Rhodococcus rhodochrous M8 (SU1731814), Rhodococcus rhodochrous M33 (VKM Ac-1515D), or Rhodococcus rhodochrous ATCC39484 (Japanese Patent Application Laid-Open No. 2001-292772), and nitrile hydratases encoded by the gene sequences thereof. Another example may be a nitrile hydratase derived from Bacillus smithii (Japanese Patent Application Laid-Open No. 09-248188). Particularly preferred examples of such a nitrile hydratase may include nitrile hydratases having amino acid sequences derived from Rhodococcus rhodochrous J-1 or Rhodococcus rhodochrous M8, and nitrile hydratases encoded by the gene sequences thereof. It is to be noted that the Rhodococcus rhodochrous M33 (VKM Ac-1515D) strain is a cell strain selected from the M8 (SU1731814) strain as a strain structurally expressing nitrile hydratase as a result of spontaneous mutation. The amino acid sequence and gene sequence of the above nitrile hydratase do not comprise a mutation (U.S. Pat. No. 5,827,699).

The term "improvement of heat resistance" is used herein to mean that the remaining activity of a heat-treated enzyme derived from a mutant strain is higher than that of a heat-treated enzyme derived from a parent strain at a level of 10% or more. The term "remaining activity" is used to mean the ratio between the amount of an amide compound generated in activity measuring using a heat-treated cell mass, and the amount of amide compound generated in activity measuring using an equal amount of an untreated cell mass. As a heat treatment method, a culture solution or a cultured cell mass that has been collected and washed may be placed in a vessel, and such a vessel may be then placed in a heating apparatus such as a water bath or incubator, followed by incubation for a certain period of time. At this time, it may also be possible to add a nitrile compound or an amide compound to enhance the stability of an enzyme before performing a heat treatment. In order to determine conditions for performing such a heat treatment, it is preferable that a treating temperature and a treating time be determined as appropriate, and that conditions for decreasing the activity of a parent strain to 50% or less be determined. Specifically, a heat treatment is performed within a range between 50° C. and 70° C. for 5 to 30 minutes. As an untreated cell mass, a culture solution, or a cultured cell mass that has been collected and washed, is cooled at 4° C. and is then used. For activity measurement, a heat-treated or untreated cell mass is used. A nitrile compound used as a substrate is allowed to come into contact with the above cell mass, and it is converted to an amide compound corresponding thereto. The amide compound is then quantified. As a substrate, any type of nitrile compound can be used, as long as nitrile hydratase reacts therewith. A preferred example for a substrate is acrylonitrile. As reaction conditions, the concentration of a substrate is set at 2.5%, the reaction temperature is set between 10° C. and 30° C., and the reaction time is set within a range between 10 and 30 minutes, for example. Phosphoric acid is added to the reaction system to terminate the enzyme reaction, and the generated acrylamide is then analyzed by HPLC or gas chromatography.

The improved nitrile hydratase of the present invention is obtained, for example, by modifying the amino acid sequence of a nitrile hydratase derived from the *Rhodococus rhodochrous* J-1 strain and then comparing the activity of the above nitrile hydratase with the nitrile hydratase activity of a parent strain to select an improved nitrile hydratase having an improved heat resistance. Examples of a modification method adopted herein may include: a method of allowing a mutation source such as hydroxylamine or nitrous acid to come into contact with the J1 strain, or acting such a mutation source on the J1 strain; a method of inducing a mutation with ultraviolet irradiation, and a method of randomly introducing a mutation into a gene encoding a nitrile hydratase derived from the J1 strain (hereinafter referred to as a nitrile hydratase gene) using PCR.

In the present invention, the inventor has found an improved nitrile hydratase wherein asparagine at position 167 has been substituted with serine in the amino acid sequence (SEQ ID NO: 2, for example) of the β subunit of a wild-type nitrile hydratase. In the present invention, in addition to such an improved nitrile hydratase, other improved nitrile hydratases having an improved heat resistance have also been selected. As a selection method, a mutant (mutant gene) corresponding to the aforementioned definition as "heat resistance" has been selected.

An example of the thus obtained enzyme is a protein, which has an amino acid sequence wherein at least one amino acid residue selected from among the phenylalanine residue at position 24, the isoleucine residue at position 88, the glutamic acid residue at position 92, the glutamic acid residue at position 93, the histidine residue at position 96, the glutamic acid residue at position 103, the asparagine residue at position 167, and the tyrosine residue at position 225, is substituted with another amino acid residue in the amino acid sequence (SEQ ID NO: 2, for example) of the β subunit of a nitrile hydratase.

In addition, another example of such an enzyme is a protein, which has an amino acid sequence wherein at least one amino acid residue selected from among the asparagine residue at position 42, the alanine residue at position 80, the alanine residue at position 118, and the aspartic acid residue at position 132, is substituted with another amino acid residue in the amino acid sequence (SEQ ID NO: 4, for example) of the α subunit of a nitrile hydratase.

Moreover, the present invention also relates to a protein, which has an amino acid sequence wherein with another amino acid residue at least one amino acid residue selected from among the leucine residue at position 144 and the valine residue at position 219 in the amino acid sequence of the β subunit and the valine residue at position 129 and the leucine residue at position 196 in the amino acid sequence (SEQ ID NO: 4) of the α subunit is substituted, wherein the amino acid sequence of the β subunit comprises a substitution of the asparagine residue at position 167 with another amino acid residue in the amino acid sequence (SEQ ID NO: 2) of the β subunit of a wild-type nitrile hydratase, and which has a heat-resistant nitrile hydratase activity.

As a means for producing the aforementioned complex mutant, any type of method may be applied. Examples of a method for producing a complex mutant may include a method of generating a site-directed substitution using a synthetic single-stranded oligonucleotide, and a method of cleaving a DNA fragment comprising several different single mutation sites with restriction enzymes and then ligating them to one another.

In addition to the aforementioned mutation, one or more (one or several, for example) amino acids may be substituted, deleted, and/or added, unless heat resistance is impaired. For example, one or two amino acid residues of the amino acid sequence (SEQ ID NO: 2, for example) of the β subunit of a wild-type nitrile hydratase, or of the amino acid sequence (SEQ ID NO: 4, for example) of the α subunit thereof may be substituted with other amino acid residues. Otherwise, one or two amino acid residues of an amino acid sequence encoded by the nucleotide sequence (SEQ ID NO: 3, for example) of a gene encoding the β subunit of a wild-type nitrile hydratase, or an amino acid sequence encoded by the nucleotide sequence (SEQ ID NO: 3, for example) of a gene encoding the α subunit thereof, may be substituted with other amino acid residues.

Next, preferred embodiments of an amino acid mutation will be described. In the present invention, as a matter of convenience, the embodiment of a mutation can be explained using a single-letter amino acid code and an amino acid number that indicates the location in the amino acid sequence of α or β subunit. For example, the wording "Fβ24L" is used to mean "a mutation whereby phenylalanine that is the amino acid at position 24 is substituted with leucine in the amino acid sequence of β subunit (SEQ ID NO: 2, for example)." Moreover, the wording "Nβ167S" is used to mean "a mutation whereby asparagine that is the amino acid at position 167 is substituted with serine in the amino acid sequence of β subunit (SEQ ID NO: 2, for example)."

Embodiment Regarding Mutation and Substitution
(1)

In this embodiment, at least one amino acid residue of the α or β subunit of a nitrile hydratase is mutated.

Single Mutation

1. Fβ24L
2. Iβ88F
3. Eβ92K
4. Eβ93G
5. Hβ96R
6. Eβ103D
7. Nβ167S
8. Yβ225H
9. Nα42D
10. Aα80T
11. Aα118V
12. Dα132N

Complex Mutation
1. Eβ93G, Eβ103D
2. Eβ93G, Dα132N
3. Hβ96R, Nα42D
4. Eβ92K, Aα80T The following nucleotide substitutions are carried out, when the aforementioned amino acid substitutions are generated. It is to be noted that gene DNAs shown in SEQ ID NOS: 1 and 3 are used as those encoding β and α subunits, respectively.

Single mutation 1: the nucleotide sequence portion "TTC" corresponding to positions 70 to 72 in the nucleotide sequence shown in SEQ ID NO: 1 is substituted with CTT, CTC, CTA, or CTG. It is particularly preferable that T at position 70 be substituted with C (TTC→CTC).

Single mutation 2: the nucleotide sequence portion "ATC" corresponding to positions 262 to 264 in the nucleotide sequence shown in SEQ ID NO: 1 is substituted with TTT or TTC. It is particularly preferable that A at position 262 be substituted with T (ATC→TTC).

Single mutation 3: the nucleotide sequence portion "GAA" corresponding to positions 274 to 276 in the nucleotide sequence shown in SEQ ID NO: 1 is substituted with AAA or AAG. It is particularly preferable that G at position 274 be substituted with A (GAA→AAA).

Single mutation 4: the nucleotide sequence portion "GAG" corresponding to positions 277 to 279 in the nucleotide sequence shown in SEQ ID NO: 1 is substituted with GGG, GGC, GGA, or GGT. It is particularly preferable that A at position 278 be substituted with G (GAG→GGG).

Single mutation 5: the nucleotide sequence portion "CAC" corresponding to positions 286 to 288 in the nucleotide sequence shown in SEQ ID NO: 1 is substituted with CGC, CGG, CGA, or CGT. It is particularly preferable that A at position 287 be substituted with G (CAC→CGC).

Single mutation 6: the nucleotide sequence portion "GAG" corresponding to positions 307 to 309 in the nucleotide sequence shown in SEQ ID NO: 1 is substituted with GAC or GAT. It is particularly preferable that G at position 309 be substituted with T (GAG→GAT).

Single mutation 7: the nucleotide sequence portion "AAC" corresponding to positions 499 to 501 in the nucleotide sequence shown in SEQ ID NO: 1 is substituted with AGC or AGT. It is particularly preferable that A at position 500 be substituted with G (AAC→AGC).

Single mutation 8: the nucleotide sequence portion "TAC" corresponding to positions 673 to 675 in the nucleotide sequence shown in SEQ ID NO: 1 is substituted with CAC or CAT. It is particularly preferable that T at position 673 be substituted with C (TAC→CAC).

Single mutation 9: the nucleotide sequence portion "AAC" corresponding to positions 124 to 126 in the nucleotide sequence shown in SEQ ID NO: 3 is substituted with GAC or GAT. It is particularly preferable that A at position 124 be substituted with G (AAC→GAC).

Single mutation 10: the nucleotide sequence portion "GCC" corresponding to positions 238 to 240 in the nucleotide sequence shown in SEQ ID NO: 3 is substituted with ACC, ACG, ACA, or ACT. It is particularly preferable that G at position 238 be substituted with A (GCC→ACC).

Single mutation 11: the nucleotide sequence portion "GCC" corresponding to positions 352 to 354 in the nucleotide sequence shown in SEQ ID NO: 3 is substituted with GTC, GTG, GTA, or GTT. It is particularly preferable that C at position 353 be substituted with T (GCC→GTC).

Single mutation 12: the nucleotide sequence portion "GAC" corresponding to positions 394 to 396 in the nucleotide sequence shown in SEQ ID NO: 3 is substituted with AAC or AAT. It is particularly preferable that G at position 394 be substituted with A (GAC→AAC).

The nucleotide substitutions of complex mutations 1 to 4 are the same as those of single mutations.

Embodiment Regarding Mutation and Substitution (2)

In this embodiment, at least two portions in the amino acid sequence of the β subunit of a nitrile hydratase are mutated, or at least one portion in the amino acid sequence of the β subunit thereof and at least one portion in the amino acid sequence of the α subunit thereof are mutated.

1. Nβ167S, Lβ144H
2. Nβ167S, Vβ219A
3. Nβ167S, Vα129A
4. Nβ167S, Lβ144H, Vβ219A
5. Nβ167S, Lβ144H, Vβ219A, Vα129A, Lα196P

The following nucleotide substitutions are carried out, when the aforementioned amino acid substitutions are generated.

Nβ167S: The nucleotide sequence portion "AAC" corresponding to positions 499 to 501 in the nucleotide sequence shown in SEQ ID NO: 1 is substituted with AGC or AGT. It is particularly preferable that A at position 500 be substituted with G (AAC→AGC).

Lβ144H: The nucleotide sequence portion "CTC" corresponding to positions 430 to 432 in the nucleotide sequence shown in SEQ ID NO: 1 is substituted with CAC or CAT. It is particularly preferable that T at position 431 be substituted with A (CTC→CAC).

Vβ219A: The nucleotide sequence portion "GTC" corresponding to positions 655 to 657 in the nucleotide sequence shown in SEQ ID NO: 1 is substituted with GCT, GCC, GCA, or GCG. It is particularly preferable that T at position 656 be substituted with C (GTC→GCC).

Vα129A: The nucleotide sequence portion "GTG" corresponding to positions 385 to 387 in the nucleotide sequence shown in SEQ ID NO: 3 is substituted with GCT, GCC, GCA, or GCG. It is particularly preferable that T at position 386 be substituted with C (GTG→GCG).

Lα196P: The nucleotide sequence portion "CTC" corresponding to positions 586 to 588 in the nucleotide sequence shown in SEQ ID NO: 3 is substituted with CCT, CCC, CCA, or CCG. It is particularly preferable that T at position 587 be substituted with C (CTC→CCC).

Embodiment Regarding Mutation and Substitution (3)

In this embodiment, at least the amino acid residue at position 26 or 48 in the amino acid sequence of the β subunit of a nitrile hydratase is substituted with another amino acid.

That is to say, the present invention provides a nitrile hydratase having an improved reactivity to aromatic nitrile and/or an improved heat resistance. The term "nitrile hydratase" is used to mean an enzyme that catalyzes a hydration reaction to convert a nitrile compound to an amide compound corresponding thereto ($RCN + 2H_2O \rightarrow RCONH_2$).

The expression "nitrile hydratase having an improved reactivity to aromatic nitrile" is used herein to mean a nitrile hydratase having a specific activity to 3-cyanopyridine that is improved at a level of 1.5 times or more.

As a method of selecting such a nitrile hydratase, a mutant (mutant gene) corresponding to the aforementioned definition regarding "mutation" is selected.

The enzyme obtained by the aforementioned means, which has an improved reactivity to aromatic nitrile, is a protein having an amino acid sequence wherein the tryptophan residue at position 48 is substituted with another amino acid residue in the amino acid sequence shown in SEQ ID NO: 2 (β subunit).

In addition, the enzyme having an improved heat resistance is a protein having an amino acid sequence wherein the histidine residue at position 26 is substituted with another amino acid residue in the amino acid sequence shown in SEQ ID NO: 2 (β subunit).

When tryptophan at position 48 in the amino acid sequence shown in SEQ ID NO: 2 (the amino acid sequence of the β subunit of a wild-type nitrile hydratase) is substituted with arginine, not only the effect of the heat resistance of the nitrile hydratase is improved, but also the reactivity to 3-cyanopyridine (an aromatic nitrile) is improved in the substrate specificity to acrylonitrile (a short chain aliphatic nitrile).

Next, preferred embodiments of an amino acid mutation will be described. For example, the wording "Wβ48R" is used to mean "a mutation whereby tryptophan that is the amino acid residue at position 48 of the β subunit (SEQ ID NO: 1) is substituted with arginine."

(1) Mutation regarding the improvement of reactivity to aromatic nitrile
  Wβ48R (2) Mutation regarding the improvement of heat resistance
  Hβ26R (3) Complex mutation
  Wβ48R, Hβ26R The following nucleotide substitutions are carried out, when the aforementioned amino acid substitutions are generated.

Wβ48R: The nucleotide sequence portion "TGG" at positions 142 to 144 is substituted with CGT, CGC, CGA, CGG, AGA, or AGG in the SEQ ID NO: 1. It is particularly preferable that T at position 142 be substituted with C (TGG→CGG).

Hβ26R: The nucleotide sequence portion "CAC" at positions 76 to 78 is substituted with CGT, CGC, CGA, CGG, AGA, or AGG in the SEQ ID NO: 1. It is particularly preferable that A at position 77 be substituted with G (CAC→CGC).

<Complex Mutation>

Moreover, it is also possible to combine several types of mutations described in the aforementioned "embodiment regarding mutation and substitution" (1) to (3) sections with one another to produce a complex mutant, thereby producing a mutant enzyme having the both properties above.

Any types of means for producing a complex mutant may be applied. Examples of such a method for producing a complex mutant may include: a method of generating a site-directed substitution using a synthetic single-stranded oligonucleotide; and a method of cleaving a DNA fragment comprising several different single mutation sites with restriction enzymes and then ligating to one another.

In addition to the aforementioned mutation, a deletion, substitution, addition, or the like of an amino acid sequence may occur, unless the properties of the mutation are impaired. For example, one or several amino acid residues, for example 1 to 10 amino acid residues, or preferably 1 to 5 amino acid residues, in the amino acid sequence that has been mutated as described above, may be deleted. Or, one or several amino acid residues, for example 1 to 10 amino acid residues, or preferably 1 to 5 amino acid residues, may be added to the amino acid sequence that has been mutated as described above. Otherwise, one or several amino acid residues, for example 1 to 10 amino acid residues, and preferably 1 to 5 amino acid residues, in the amino acid sequence that has been mutated as described above, may be substituted with other amino acid residues.

<Mutagenesis Methods>

A nitrile hydratase gene, into which the aforementioned single mutation or complex mutation has been introduced, can be prepared by known methods such as the Kunkel method or the Gapped duplex method, using a mutation introduction kit that utilizes the site-directed mutagenesis, such as the QuikChange XL Site-Directed Mutagenesis Kit (Stratagene), the GeneTailor™ Site-Directed Mutagenesis System (manufactured by Invitrogen), or the TaKaRa Site-Directed Mutagenesis System (Mutan-K, Mutan-Super Express Km, or the like; manufactured by Takara Bio) [Nucleic. Acid. Res. 10, 6487 (1982), Molecular Cloning 2nd Edt, Cold Spring Harbor Laboratory Press (1989)].

It is considered that nitrile hydratases other than that of the J1 strain are also improved in terms of heat resistance, depending on the position of the aforementioned mutation, and the type of the aforementioned amino acid and DNA sequence to be mutated. Examples of such a strain may include the aforementioned *Rhodococcus rhodochrous* M8 (SU1731814), *Rhodococcus rhodochrous* M33 (VKM Ac-1515D), *Rhodococcus rhodochrous* ATCC39484 (Japanese Patent Application Laid-Open No. 2001-292772), and *Bacillus smithii* (Japanese Patent Application Laid-Open No. 09-248188).

Further, DNA that is capable of hybridizing with DNA consisting of a nucleotide sequence complementary to a nucleotide sequence wherein mutation is introduced into the aforementioned nucleotide sequence shown in SEQ ID NO: 1 or 3 under stringent conditions is also included in the gene DNA of the present invention. Stringent conditions mean that the salt (sodium) concentration is between 150 and 900 mM and that the temperature is between 55° C. and 75° C., for example, and preferably mean that the salt (sodium) concentration is between 250 and 450 mM and that the temperature is 68° C.

<Resistance to Amide Compound>

The improved nitrile hydratase of the present invention further has a property regarding resistance to an amide compound. The term "resistance to an amide compound" is used herein to mean that a nitrile hydratase activity can be maintained in the presence of an amide compound, when compared with nitrile hydratases derived from other wild-type strains. The type of an amide compound, to which the mutant nitrile hydratase of the present invention is resistant, is not particularly limited. An example of such an amide compound is an amide compound shown in the following chemical formula:

$$R-CONH_2$$

(wherein R represents a substituted or unsubstituted alkyl group, a substituted or unsubstituted alkenyl group, a substituted or unsubstituted cycloalkyl group, a substituted or unsubstituted aryl group, or a substituted or unsubstituted saturated or unsaturated heterocyclic group). An acrylamide wherein R is $CH_2=CH$ in the above formula is particularly preferable.

Resistance to an amide compound can be evaluated, for example, by analyzing the consumption or consumption rate of a nitrile compound such as acrylonitrile acting as a substrate, when the culture of a transformant having the improved nitrile hydratase of the present invention or a nitrile hydratase isolated from the transformant is under the presence of an amide compound such as acrylamide (a high concentration between 30% and 50%, for example). Thereafter, when the above nitrile hydratase is compared with a nitrile hydratase derived from a patent strain, if the above consumption or consumption rate exceeds 1.1 times, for example, it can be evaluated that it is resistant to the amide compound.

<Preparation of Recombinant Vector and Transformant (or Transductant)>

A method of preparing a recombinant vector comprising the aforementioned nitrile hydratase gene and a transformant (or transductant) will be described.

It is necessary that a nitrile hydratase gene be incorporated into a vector, such that it is allowed to express in a host organism to be transformed or transduced.

Examples of a vector may include plasmid DNA, bacteriophage DNA, retrotransposon DNA, and artificial chromosome DNA.

Examples of a host used herein may include bacteria such as *Escherichia coli* or *Bacillus subtilis*, yeasts, animal cells, insect cells, and plant cells.

When *Escherichia coli* is used as a host, it is preferable to use an expression vector having high expression efficiency, such as the expression vector pKK233-2 having a trc promoter (manufactured by Amersham Biosciences) or pTrc99A (manufactured by Amersham Biosciences).

A promoter, a terminator, an enhancer, a splicing signal, a poly (A) addition signal, a selective marker, a ribosome-binding sequence (SD sequence), or the like as well as a nitrile hydratase gene, can be ligated to such a vector. Examples of a selective marker may include a kanamycin-resistant gene, a dihydrofolate reductase gene, an ampicillin-resistant gene, and a neomycin-resistant gene.

The type of a host and a method of introducing a recombinant vector into a host will be described below.

When a bacterium is used as a host, an example of *Escherichia coli* is *Escherichia coli*. Examples of the *Rhodococcus* strain may include *Rhodococcus rhodochrous* ATCC12674, *Rhodococcus rhodochrous* ATCC17895, and *Rhodococcus rhodochrous* ATCC19140. These ATCC strains can be acquired from the American Type Culture Collection.

The type of a method of introducing a recombinant vector into bacteria is not particularly limited, as long as it is a method of introducing DNA into bacteria. Examples of such an introduction method may include a method using calcium ions and the electroporation method.

When yeast is used as a host, *Saccharomyces cerevisiae*, *Schizosaccharomyces pombe*, *Pichia pastoris*, or the like, is used. The type of a method of introducing a recombinant vector into yeast is not particularly limited, as long as it is a method of introducing DNA into yeast. Examples of such an introduction method may include the electroporation method, the spheroplast method, and the lithium acetate method.

When an animal cell is used as a host, monkey cell COS-7, Vero, CHO cell, mouse L cell, rat GH3, human FL cell, or the like, is used. Examples of a method of introducing a recombinant vector into such an animal cell may include the electroporation method, the calcium phosphate method, and the lipofection method.

When an insect cell is used as a host, Sf9 cell, Sf21 cell, or the like, is used. Examples of a method of introducing a recombinant vector into such an insect cell may include the calcium phosphate method, the lipofection method, and the electroporation method.

When a plant cell is used as a host, tobacco BY-2 cell or the like is used. However, examples are not limited thereto. Examples of a method of introducing a recombinant vector into such a plant cell may include the *Agrobacterium* method, the particle gun method, the PEG method, and the electroporation method.

<Production of Nitrile Hydratase>

Next, nitrile hydratase and a production method thereof will be described.

The nitrile hydratase of the present invention can be obtained by culturing a transformant (or transductant) comprising the nitrile hydratase gene prepared by the aforementioned method and then collecting the enzyme from the culture.

The term "culture" is used herein to mean any one of a culture supernatant, cultured cells or a cultured cell mass, and a product obtained by disrupting cells or a cell mass.

The culture of the transformant (or transductant) of the present invention is carried out by a common method used in the culture of a host described below.

Either a natural medium or a synthetic medium can be used as a medium that is used for the culture of a transformant obtained using a microorganism such as *Escherichia coli* or yeast as a host, as long as it contains a carbon source, a nitrogen source, inorganic salts, or the like, that can be assimilated by microorganisms, and as long as the culture of a transformant can efficiently be carried out therein. Examples of a carbon source may include: carbohydrate such as glucose, fructose, sucrose, or starch; organic acid such as acetic acid or propionic acid; and alcohol such as ethanol or propanol. Examples of a nitrogen source may include: ammonium salts of inorganic acid or organic acid, such as ammonia, ammonium chloride, ammonium sulfate, ammonium acetate, or ammonium phosphate; other nitrogen-containing compounds; peptone; meat extract; and corn steep liquor. Examples of an inorganic material may include monopotassium phosphate, dipotassium phosphate, magnesium phosphate, magnesium sulfate, sodium chloride, ferrous sulfate, manganese sulfate, copper sulfate, and calcium carbonate. Culture is carried out at a temperature between 30° C. and 40° C. under aerobic conditions such as a shaking culture or aeration-agitation culture. The pH is controlled using inorganic or organic acid, an alkaline solution, or the like. Antibiotics such as ampicillin or tetracycline may be added to a medium during the culture as necessary.

Moreover, cobalt ions or iron ions, which are prosthetic metals for nitrile hydratase, may be added to a medium, and further nitrites or amides acting as derivatives for the enzyme may also be added thereto.

When microorganisms that have been transformed with an expression vector comprising an inducible promoter as a promoter are cultured, an inducer may be added to a medium as necessary. For example, when microorganisms transformed with an expression vector comprising a promoter capable of being induced by isopropyl-β-D-thiogalactoside (IPTG) are cultured, IPTG or the like may be added to a medium. In addition, when microorganisms transformed with an expression vector comprising a trp promoter capable of being induced by indoleacetic acid (IAA) are cultured, IAA or the like may be added to a medium.

Examples of a medium used for the culture of a transformant obtained using an animal cell as a host may include commonly used RPMI1640 medium, DMEM medium, and a medium obtained by adding fetal bovine serum or the like to these media. Culture is generally carried out in the presence of 5% CO$_2$ at 37° C. for 1 to 30 days. Antibiotics such as kanamycin or penicillin may be added to a medium during the culture as necessary.

As a method of collecting a nitrile hydratase from a culture, a cell mass or cells are disintegrated by sonication, repeated cycles of freezing and thawing, a treatment by a homogenizer, or the like to collect a protein of interest.

When a transformant is a plant cell or plant tissue, culture is carried out using a medium that is commonly used for plant culture, such as MS basal medium or LS basal medium. Either a common solid culture method or a liquid culture method can be adopted as a culture method.

As a method of collecting a nitrile hydratase from a culture, cells are first destroyed by a cell lysis treatment using an enzyme such as cellulase or pectinase, an ultrasonic disintegration treatment, a trituration method, or the like. Thereafter, insoluble matters are eliminated by filtration, centrifugation, or the like to obtain a crude protein solution. In order to purify the protein of the present invention form the aforementioned crude solution, salting-out, various types of chromatographies (for example, gel filtration chromatography, ion exchange chromatography, affinity chromatography, etc.), SDS polyacrylamide gel electrophoresis, and the like, are performed singly or in combination as appropriate.

In addition, when the protein of the present invention is produced at the outside of a cell mass or a cell, a culture solution is directly used, or such a cell mass or a cell is eliminated by centrifugation or the like. Thereafter, common biochemical methods used for isolation and purification of proteins, such as ammonium sulfate precipitation, gel chromatography, ion exchange chromatography, or affinity chromatography, are performed singly or in combination as appropriate to isolate and purify the protein of the present invention from the aforementioned culture.

Moreover, in the present invention, it is also possible to collect a protein of interest through a gene DNA encoding the mutant nitrile hydratase of the present invention or the aforementioned vector by employing a cell-free protein synthetic system, using no living cells.

Such a cell-free protein synthetic system is a system for synthesizing proteins in an artificial vessel such as a test tube using a cell extract. It reads information obtained from mRNA and synthesizes a protein on a ribosome, for example. It is to be noted that the cell-free protein synthetic system used in the present invention includes a cell-free transcription system for synthesizing RNA using DNA as a template.

As the aforementioned cell extract, an extract derived from eukaryotic cells or prokaryotic cells, such as an extract from wheat germ, rabbit reticulocytes, mouse L-cells, HeLa cells, CHO cells, budding yeast, *Escherichia coli*, etc., can be used. It is to be noted that such a cell extract may be concentrated or may not be concentrated.

Herein, genetic information encoded on DNA is transcribed, so that it is converted to mRNA by transcription. Thereafter, it is then translated, so that it is further converted to a protein. In order to reproduce such a translation process in an artificial vessel to synthesize a protein, it is necessary that a group of translation factors such as ribosome, tRNA, or various types of protein factors, be stabilized, and that a system for producing mRNA be constructed depending on purpose. A cell extract can be obtained by ultrafiltration, dialysis, polyethylene glycol (PEG) precipitation, or the like, for example.

In the present invention, a cell-free protein can also be synthesized using a commercially available kit. Examples of such a kit may include PROTEIOS™ (Toyobo) and TNT™ System (Promega) for a reagent kit, PG-Mate™ (Toyobo) and RTS (Roche Diagnostics) for a synthetic device.

A mutant nitrile hydratase obtained by the cell-free protein synthesis can be purified by appropriately selecting chromatography. Moreover, isolation and purification of such a mutant nitrile hydratase can be confirmed by SDS-PAGE or the like. Furthermore, the activity of the enzyme can be measured by measuring the conversion rate to convert a nitrile compound to an amide compound.

<Production of Amide Compound>

Next, a method for producing an amide compound using a transformant (or transductant) will be described.

The culture, enzyme, or the like obtained by the aforementioned culture method is used as a biocatalyst when a nitrile compound is converted to an amide compound corresponding thereto. A nitrile compound used as a substrate for a conversion reaction is appropriately selected depending on the substrate specificity of a biocatalyst. In the case of a nitrile hydratase derived from the *Rhodococcus rhodochrous* J-1 strain for example, a preferred substrate therefor is acrylonitrile.

The usage embodiment and reaction embodiment of a biocatalyst is appropriately selected depending on the type of the biocatalyst or the like. For example, as the usage embodiment of a biocatalyst, the aforementioned culture or purified enzyme may be directly used, or they may be supported by a suitable carrier and may be used in the form of an immobilized enzyme.

EXAMPLES

The present invention will be further specifically described in the following examples. However, these examples are not intended to limit the scope of the present invention. It is to be noted that the *Rhodococcus rhodochrous* J-1 strain was deposited with International Patent Organism Depositary, National Institute of Advanced Industrial Science and Technology, Independent Administrative Institution (at Tsukuba Central 6, 1-1-1 Higashi, Tsukuba, Ibaraki, Japan) under accession No. FERM BP-1478 (original deposition date: Sep. 18, 1987).

Example 1

Obtainment of Improved Nitrile Hydratase Gene (I)

(1) Preparation of Chromosomal DNA

The *Rhodococcus rhodochrous* J-1 strain was subjected to shaking culture at 30° C. for 72 hours in 100 ml of MYK medium (0.5% polypeptone, 0.3% Bacto-yeast extract, 0.3% Bacto-malt extract, 1% glucose, 0.2% K$_2$HPO$_4$, 0.2% KH$_2$PO$_4$, pH7.0).

After completion of the culture, cells were collected, and the obtained cell mass was then suspended in 4 ml of saline-EDTA solution (0.1 M EDTA, 0.15 M NaCl (pH8.0)). Thereafter, 8 mg of lysozyme was added to the obtained suspension, and the mixture was shaken at 37° C. for 1 to 2 hours. Thereafter, the resultant was frozen at −20° C.

Subsequently, 10 ml of Tris-SDS solution (1% SDS, 0.1 M NaCl, 0.1 M Tris-HCl (pH9.0)) was added thereto, while it was gently shaken. Thereafter, proteinase K (Merck) (final concentration: 0.1 mg) was added thereto, and the obtained mixture was then shaken at 37° C. for 1 hour.

Subsequently, an equal amount of TE saturated phenol was added to the resultant (TE: 10 mM Tris-HCl, 1 mM EDTA (pH8.0)). The mixture was stirred, and was then centrifuged.

An upper layer was collected, and two times its volume of ethanol was added thereto. Thereafter, DNA was reeled off using a glass rod, and the phenol was successively removed with 90%, 80%, and 70% ethanols.

Thereafter, DNA was dissolved in 3 ml of TE buffer solution, and a ribonuclease A solution (which had been subjected to a heat treatment at 100° C. for 15 minutes) was added to the solution to a concentration of 10 µg/ml. The mixture was shaken at 37° C. for 30 minutes. Thereafter, proteinase K was further added thereto, and the obtained mixture was shaken at 37° C. for 30 minutes. Thereafter, an equal amount of TE saturated phenol was added thereto, followed by centrifugation, thereby separating it into an upper layer and a lower layer.

This operation was repeatedly performed on the upper layer two times, and an equal amount of chloroform (containing 4% isoamyl alcohol) was then added thereto. The same extraction operation was repeatedly performed thereon (hereinafter, this operation is referred to as a phenol treatment). Thereafter, to the upper layer, two times its volume of ethanol was added, and DNA was then recovered by reeling it off with a glass rod to obtain a chromosomal DNA sample.

(2) Construction of Plasmid

In order to use a wild-type nitrile hydratase gene as a control for evaluation of heat resistance, the above gene was first amplified by ordinary PCR.

The PCR was carried out using a reaction solution having the following composition under the following conditions.

It is to be noted that the restriction enzyme NcoI cleavage recognition site and the restriction enzyme HindIII cleavage recognition site were introduced into primer JH1-02 (SEQ ID NO: 5) and primer NH-17 (SEQ ID NO: 6), respectively. An amplified DNA product is cleaved with both restriction enzymes, so that it can easily be inserted between the NcoI site and HindIII site of an expression vector pTrc99A, which will be described later.

| <Composition of reaction solution> | |
| --- | --- |
| Template DNA (chromosomal DNA) | 1 µl |
| 10× ExTaq Buffer (manufactured by Takara Shuzo Co., Ltd.) | 10 µl |
| Primer JH1-02 | 1 µl |
| Primer NH-17 | 1 µl |
| 2.5 mM dNTP mix | 8 µl |
| Sterilized water | 78 µl |
| ExTaq DNA polymerase (manufactured by Takara Shuzo Co., Ltd.) | 1 µl |

```
<Primers>
                                          (SEQ ID NO: 5)
JH1-02:        GGAATGAGGCCATGGATGGTATCC (SEQ ID NO: 6)
NH-17:         GCGTAAGCTTCCGCGAGATCAGTATCCACCG
```

The PCR was carried out by performing 30 cycles of (94° C., 30 seconds; 65° C., 30 seconds; and 72° C., 3 minutes) using Thermalcycler personal (Takara Shuzo).

After completion of the PCR, 5 µl of the reaction solution was subjected to 0.7% agarose gel electrophoresis, and a 3 kb amplified fragment was detected. After completion of the reaction, the obtained reaction solution was purified by GFX column (Amersham Biosciences), followed by cleavage with the restriction enzymes NcoI and HindIII. The PCR product that had been treated with the restriction enzymes was subjected to 0.7% agarose gel electrophoresis to recover a band around 3 kb. The recovered PCR product was ligated to a vector (the NcoI-HindIII site of pTrc99A) using Ligation Kit (Takara Shuzo), and JM109 was then transformed therewith. Several clones from the obtained transformant colony were inoculated into 1.5 ml of LB-Amp medium, and the medium was then subjected to shaking culture at 37° C. for 12 hours. After completion of the culture, the culture was collected by centrifugation, and plasmid DNA was then extracted using Flexi Prep (manufactured by Amersham Biosciences). The obtained plasmid DNA was cleaved with the restriction enzymes NcoI and HindIII, and the cleaved DNA portion was then subjected to 0.7% agarose gel electrophoresis for confirmation. Thereafter, a clone, to which a nitrile hydratase gene fragment (3 kb) was properly ligated, was selected. The selected clone was named as pJH601 (FIG. 1). JM109 was transformed with the pJH601 (JM109/pJH601).

The plasmid pJH601 is an expression plasmid for a wild-type nitrile hydratase. It was deposited with International Patent Organism Depositary, National Institute of Advanced Industrial Science and Technology, Independent Administrative Institution (at Tsukuba Central 6, 1-1-1 Higashi, Tsukuba, Ibaraki, Japan) under accession No. FERM ABP-10314 (original deposition date: Dec. 26, 2002).

(3) Construction of Mutant Gene Library

Based on the plasmid pJH601 obtained in the aforementioned process (2), random mutagenesis was carried out to a wild-type nitrile hydratase gene. For the mutagenesis, nucleotide substitution due to incorrect incorporation of nucleotides by PCR was utilized. The PCR was carried out using a reaction solution having the following composition under the following reaction conditions.

| <Composition of reaction solution> | |
| --- | --- |
| Template DNA (pJH601 prepared in the aforementioned process) | 1 µl |
| 10× PCR buffer (manufactured by GIBCO) | 10 µl |
| 50 mM MgCl$_2$ (manufactured by GIBCO) | 3 µl |
| Primer Trc-02 | 1 µl |
| Primer Trc-03 | 1 µl |
| 2.5 mM dNTP mix | 8 µl |
| 10 mM dITP | 2 µl |
| 10 mM dBraUTP | 2 µl |
| Sterilized water | 71 µl |
| Taq DNA polymerase (manufactured by GIBCO) | 1 µl |

```
<Primers>
TRC-02:
GGAATTCGTATAATGTGTGGAATTGTGAGC     (SEQ ID NO: 7)

TRC-03:
GGCTGAAAATCTTCTCTCATCCGCC          (SEQ ID NO: 8)
```

The PCR was carried out by performing 30 cycles of (94° C., 30 seconds; 65° C., 30 seconds; and 72° C., 3 minutes) using Thermalcycler personal (Takara Shuzo).

After completion of the PCR, 5 µl of the reaction solution was subjected to 0.7% agarose gel electrophoresis, and a 3 kb amplified fragment was detected. After completion of the reaction, the obtained reaction solution was purified by GFX column (Amersham Biosciences), followed by cleavage with the restriction enzymes NcoI and HindIII. The PCR product that had been treated with the restriction enzymes was subjected to 0.7% agarose gel electrophoresis to recover a band around 3 kb. The recovered PCR product was ligated to a vector (the NcoI-HindIII site of pTrc99A) using Ligation Kit (Takara Shuzo), and JM109 was then transformed with the thus ligated product.

(4) Screening of Heat-Resistant Nitrile Hydratase and Identification of Mutated Site Each of the JM109 transformant comprising a mutant nitrile hydratase gene obtained in the aforementioned process (3) and JM109/pJH601 was inoculated into a 96-well deep well plate, in which 1 ml of LB-Amp medium (containing 1 mM IPTG and 5 μg/ml CoCl$_2$) had been placed, and it was then subjected to liquid culture at 37° C. for 12 hours. Thereafter, the obtained culture was subjected to a heat treatment at a temperature of 55° C. for 30 minutes, and the remaining activity of the nitrile hydratase was then measured.

For activity measurement, a 50 mM phosphate buffer solution (pH 7.7) that contained 5% acrylonitrile was added in an amount equal to that of the cell mass suspension, and the reaction was then carried out at 30° C. for 30 minutes. Thereafter, an equal amount of 0.1 M phosphoric acid was added to the reaction solution, and the reaction was terminated. Thereafter, the cell mass was eliminated by centrifugation, the supernatant was then subjected to HPLC, and the concentration of the generated acrylamide was then analyzed (WAKO-SIL 5C8 (Wako Pure Chemical Industries, Ltd.); 10% acetonitrile containing 5 mM phosphoric acid; the flow rate of a mobile phase: 1 ml/min.; and ultraviolet absorption detector wave length: 260 nm). An untreated cell mass, which had not been subjected to a heat treatment and had been conserved at 4° C., was used as a control for comparison, and the remaining activity thereof was obtained.

As a result of screening performed on several thousands of transformant strains, 16 strains exhibiting a remaining activity that was higher than that of a wild-type enzyme was obtained. In addition, such cell strains were cultured, and plasmids were then recovered. Thereafter, the nucleotide sequences thereof were determined. Beckman CEQ-2000XL was used to determine the nucleotide sequences. The results are shown in Table 1.

TABLE 1

| Name of plasmid | Remaining activity (%) | Mutated site |
|---|---|---|
| pJH601 (parent strain) | 40 | None |
| P47 | 51 | Fβ24L |
| p31 | 89 | Iβ88F |
| p70 | 87 | Eβ92K |
| p3 | 85 | Eβ93G |
| p74 | 80 | Hβ96R |
| p76 | 69 | Eβ103D |
| p52 | 70 | Nβ167S |
| p40 | 68 | Yβ225H |
| p79 | 66 | Nα42D |
| p81 | 71 | Aα80T |
| p32 | 63 | Aα118V |
| p84 | 64 | Dα132N |
| p43 | 89 | (Eβ93G, Eβ103D) |
| p49 | 85 | (Eβ93G, Dα132N) |
| p2 | 80 | (Hβ96R, Nα42D) |
| p23 | 75 | (Eβ92K, Aα80T) |

Example 2

Properties of Improved Nitrile Hydratase

JM109 was retransformed with the plasmid p3 obtained in Example 1 (JM109/p3), and the obtained colony was cultured in LB medium (containing ampicillin, IPTG, and cobalt) at 37° C. overnight. A cell mass was recovered by centrifugation, and was then washed with a 50 mM phosphate buffer solution twice to obtain a cell mass suspension.

0.5 ml of the obtained cell mass suspension was placed in a test tube, and it was incubated in a water bath at each temperature of 50° C., 55° C., and 60° C., for 5 to 20 minutes. Thereafter, it was cooled on ice.

The activity of the cell mass was measured by the method described in Example 1 (4).

JM109/pJH601 was used as a control for comparison. The cell strain, which had not been subjected to a heat treatment and had been kept cold at 4° C., was defined as an untreated cell strain. The remaining activities of such strains were obtained. The results are shown in Table 2.

TABLE 2

|  | Untreated | 50° C., 20 min. | 55° C., 20 min. | 60° C., 5 min. |
|---|---|---|---|---|
| JM109/pJH601 | 100 | 54 | 9 | 6 |
| JM109/p3 | 100 | 80 | 97 | 105 |

After completion of the heat treatment at 60° C. for 5 minutes, the wild-type enzyme maintained a remaining activity of 6%. In contrast, the improved enzyme maintained a remaining activity of almost 100%. Thus, it was revealed that the improved enzyme had an improved heat resistance.

Example 3

Production of Recombinant *Rhodococcus* Stain

The properties of the improved enzyme obtained in Example 1 were confirmed using a recombinant *Rhodococcus* strain.

(1) Construction of Plasmid Used for Introduction into *Rhodococcus* Strain

A plasmid having a mutation of p3 (Eβ93G) used for introduction into a *Rhodococcus* strain was produced by the following method. In order to introduce such a mutation, site-directed mutagenesis was applied, and a commercially available kit, QuikChange XL Site-Directed Mutagenesis Kit (Stratagene) was used. The experiment was carried out in accordance with an operation manual. As a template plasmid into which such a mutation be introduced, pSJ034 was used. Such pSJ034 is a plasmid that allows nitrile hydratase to express in a *Rhodococcus* strain. The plasmid pSJ034 was produced from pSJ023 by the method described in Japanese Patent Application Laid-Open No. 10-337185. It is to be noted that pSJ023 was deposited as a transformant "*R. rhodochrous* ATCC12674/pSJ023" with International Patent Organism Depositary, National Institute of Advanced Industrial Science and Technology, Independent Administrative Institution (at Tsukuba Central 6, 1-1-1 Higashi, Tsukuba, Ibaraki, Japan) under accession No. FERM BP-6232 (original deposition date: Mar. 4, 1997).

Two types of primers used to introduce a mutation were synthesized. The underlined portion indicates a site, into which a mutation was introduced.

```
                                              (SEQ ID NO: 9)
NHM-F:  gatcatcaccgaagaagggcgaaagcaccgtgtgc (SEQ ID NO: 10)
NHM-R:  gcacacggtgctttcgcccttcttcggtgatgatc
```

In order to introduce a mutation, PCR was carried out using GeneAmp9700 (PE Bioscience). A reaction, which consisted of 95° C., 1 minute and 18 cycles of (95° C., 50 seconds; 60° C., 50 seconds; and 68° C., 20 minutes), and 68° C., 20 minutes, was carried out.

<Composition of reaction solution>

| | |
|---|---|
| pSJ034 (10 ng) | 2 μl |
| 10× reaction buffer | 5 μl |
| Primer NHM-F (100 ng/μl) | 1 μl |
| Primer NHM-R (100 ng/μl) | 1 μl |
| 2.5 mM dNTPmix | 1 μl |
| Sterilized water | 36 μl |
| QuickSolution | 3 μl |
| Pfu Turbo DNA Polymerase | 1 μl |

After completion of the PCR, 10 μl of the reaction solution was subjected to 0.7% agarose gel electrophoresis, and an approximately 11 kb amplified fragment was detected. After confirmation of the presence of the amplified fragment, 1 μl of DpnI (included with the kit) was added to the PCR reaction solution. Thereafter, a reaction was carried out at 37° C. for 1 hour, and template DNA was eliminated.

Subsequently, transformation was carried out using XL10-GOLD ultracompetent cell (included with the kit). 2 μl of the DpnI-treated PCR reaction solution was mixed with 45 μl of competent cells, and the obtained mixture was then incubated at 4° C. for 30 minutes, followed by performing heat shock at 42° C. for 30 seconds. Thereafter, 0.5 ml of NZY+ medium (1% NZ amine, 0.5% yeast extract, 0.5% NaCl, 12.5 mM $MgCl_2$, 12.5 mM $MgSO_4$, 0.4% glucose, pH 7.5) was added to the reaction product, and the obtained mixture was further cultured at 37° C. for 1 hour. 250 μl of the obtained culture solution was plated on an LB plate (1% NaCl, 1% trypton, 0.5% yeast extract, 2% agar, 50 mg/l ampicillin), and it was then cultured at 37° C. for 1 day.

Figure 2:
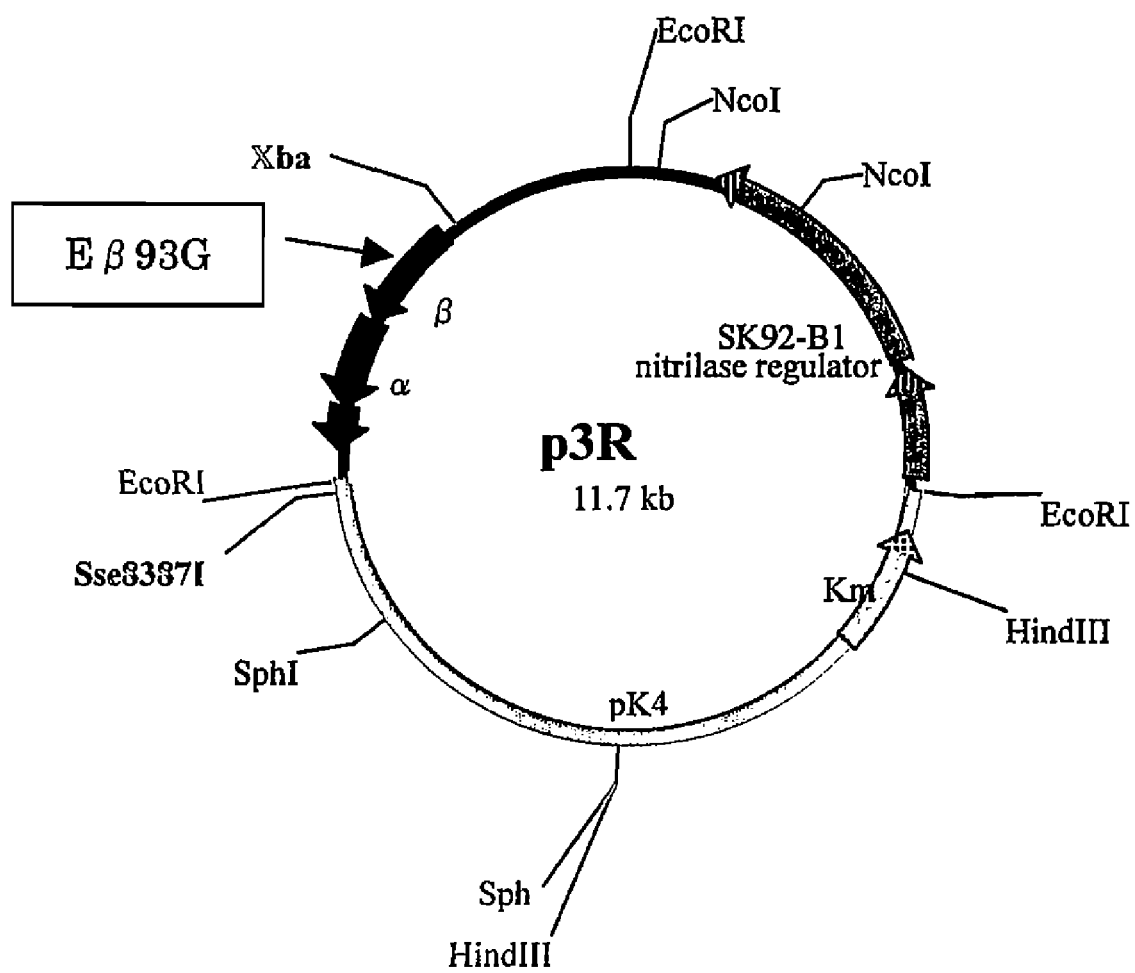
FIG. 2 is a structural view of the plasmid p3R.

Several colonies obtained as above were cultured in 1.5 ml of LB medium (50 mg/l ampicillin), and a plasmid was then prepared using FlexiPrep Kit (Amersham Biosciences). Finally, the nucleotide sequence of the obtained plasmid was determined, and thus it was confirmed that a mutation of interest had been introduced. Thus, p3R, a plasmid introduced a mutation of Eβ93G, was obtained (FIG. 2).

(2) Obtainment of Recombinant *Rhodococcus* Strain into which Mutant Enzyme Gene has been Introduced (Transformant)

The cells of *Rhodococcus rhodochrous* ATCC 12674 strain that were at the logarithmic growth phase were collected using a centrifugal separator, and they were then washed three times with ice-cold sterilized water. Thereafter, the cells were suspended in sterilized water. 1 μl of the plasmid p3R prepared in (1) above was mixed with 10 μl of the cell mass suspension, and the mixture was then cooled on ice. The suspension, which contained the DNA and the cell mass, was placed in a cuvette, and it was then subjected to an electropulse treatment at 2.0 KV at 200 OHMS using a gene transfer device, Gene Pulser (BIORAD). The electropulse-treated solution was left at rest under cooling on ice for 10 minutes, and thereafter, heat shock was performed thereon at 37° C. for 10 minutes. Thereafter, 500 μl of MYK medium (0.5% polypeptone, 0.3% Bacto-yeast extract, 0.3% Bacto-malt extract, 0.2% $K_2HPO_4$, and 0.2% $KH_2PO_4$) was added to the resultant, and the obtained mixture was then left at rest at 30° C. for 5 hours. Thereafter, the reaction solution was applied on MYK agar medium that contained 50 μg/ml kanamycin, and it was then cultured at 30° C. for 3 days. The thus obtained recombinant *Rhodococcus* strain (ATCC 12674/p3R) was inoculated into 10 ml of MYK medium (containing 50 μg/ml kanamycin), and pre-culture was then carried out at 30° C. for 72 hours. Main culture was carried out in 100 ml of MYK medium (containing 50 μg/ml kanamycin, 5 μg/ml $CoCl_2$, and 0.1% urea). 1% of the culture obtained from the pre-culture was inoculated therein, and it was then cultured at 30° C. for 96 hours. Thereafter, cells were collected by centrifugation, and the cell mass was then washed with a 100 mM phosphate buffer solution (pH 8.0). Finally, it was suspended in a small amount of buffer solution.

(3) Confirmation of Heat Resistance of Recombinant *Rhodococcus* Strain

The heat resistance of the obtained recombinant *Rhodococcus* strain was examined. As a control for comparison, ATCC12674/pSJ034 having a wild-type nitrile hydratase was prepared.

0.5 ml of the obtained cell suspension was placed in a test tube, and it was incubated in a water bath at each temperature of 65° C. and 70° C. for 10 minutes. Thereafter, it was cooled on ice. The cell, which had not been subjected to a heat treatment and had been kept cold at 4° C., was defined as an untreated cell, and it was used as a control for comparison. The remaining activities of such cells were obtained. The results are shown in Table 3.

Activity measurement was carried out by the same method as that described in Example 1(4) with the exception that the reaction was carried out at 10° C. for 10 minutes. The results are shown in Table 3.

TABLE 3

| | Untreated | 65° C., 10 min. | 70° C., 10 min. |
|---|---|---|---|
| ATCC12674/pSJ034 | 100 | 50 | 4 |
| ATCC12674/p3R | 100 | 80 | 46 |

Thus, after completion of the heat treatment at 70° C. for 10 minutes, ATCC 12674/pSJ034 maintained a remaining activity of only 4%. In contrast, ATCC 12674/p3R maintained a remaining activity of 46%. Accordingly, it was revealed that the improved enzyme had an improved heat resistance.

Example 4

Site-Directed Random Mutation

Random mutagenesis was carried out on a specific mutated site.

(1) Site-Directed Random Mutagenesis

Using the site-directed mutagenesis kit used in Example 3, a random mutation was introduced into pJH601.

As a site into which a mutation was to be introduced, the amino acid at position 93 in the amino acid sequence of the β subunit was selected, and two types of primers used for introduction of a mutation were then synthesized. The underlined portions indicate sites into which a mutation was to be introduced.

(SEQ ID NO: 11)
β93RM-F:  caagatcatcaccgaagaa<u>NNS</u>cgaaagcaccgtgtgcaag (SEQ ID NO: 12)
β93RM-R:  cttgcacacggtgctttcg<u>SNN</u>ttcttcggtgatgatcttg

N : A + T + G + C    S : G + C

PCR was carried out using GeneAmp9700 (PE Bioscience) under the following conditions. A reaction, which consisted of 95° C., 1 minute, 18 cycles of (95° C., 50 seconds; 60° C., 50 seconds; and 68° C., 14 minutes), and 68° C., 7 minute, was carried out.

<Composition of reaction solution>

| | |
|---|---|
| pJH601 (10 ng) | 2 μl |
| 10× reaction buffer | 5 μl |
| Primer β93RM-F (100 ng/μl) | 1 μl |
| Primer β93RM-R (100 ng/μl) | 1 μl |
| 2.5 mM dNTPmix | 1 μl |
| Sterilized water | 36 μl |
| QuickSolution | 3 μl |
| Pfu Turbo DNA Polymerase | 1 μl |

After completion of the PCR, 10 μl of the reaction solution was subjected to 0.7% agarose gel electrophoresis, and an approximately 6 kb amplified fragment was detected. After confirmation of the presence of the amplified fragment, 1 μl of DpnI (included with the kit) was added to the PCR reaction solution. Thereafter, a reaction was carried out at 37° C. for 1 hour, and template DNA was eliminated. Subsequently, transformation was carried out using XL10-GOLD ultracompetent cell (included with the kit). 2 μl of the DpnI-treated PCR reaction solution was mixed with 45 μl of competent cells, and the obtained mixture was then incubated at 4° C. for 30 minutes, followed by performing heat shock at 42° C. for 30 seconds. Thereafter, 0.5 ml of NZY$^+$ medium (1% NZ amine, 0.5% yeast extract, 0.5% NaCl, 12.5 mM $MgCl_2$, 12.5 mM $MgSO_4$, 0.4% glucose, pH 7.5) was added to the reaction product, and the obtained mixture was further cultured at 37° C. for 1 hour. 250 μl of the obtained culture solution was plated on an LB plate (1% NaCl, 1% trypton, 0.5% yeast extract, 2% agar, 50 mg/l ampicillin), and it was then cultured at 37° C. for 1 day.

(2) Evaluation of Site-Directed Random Mutation-Introduced Strain

Each of the colonies obtained in the aforementioned process (1) and XL10/pJH601 was inoculated into a 96-well deep well plate that contained LB-Amp medium (containing 1 mM IPTG and 5 μg/ml $CoCl_2$), followed by liquid culture at 37° C. for 12 hours. The obtained culture was subjected to a heat treatment at a temperature of 55° C. for 30 minutes. Thereafter, the remaining activity of the nitrile hydratase was measured.

Activity measurement was carried out by the same method as described in Example 1(4). The cell, which had not been subjected to a heat treatment and had been kept cold at 4° C., was defined as an untreated cell, and it was used as a control for comparison. The remaining activities of such cells were obtained.

Regarding strains having a remaining activity higher than that of the control, the nucleotide sequences thereof were then determined.

The results are shown in Table 4.

TABLE 4

Relative remaining activities of amino acid substitution products

| Name of plasmid | Relative remaining activity (%) | Nucleotide sequence | Amino acid |
|---|---|---|---|
| pJH601 | 40 | GAG | Glu |
| p3 | 85 | GGG | Gly |

TABLE 4-continued

Relative remaining activities of amino acid substitution products

| Name of plasmid | Relative remaining activity (%) | Nucleotide sequence | Amino acid |
|---|---|---|---|
| p104 | 88 | CGC | Arg |
| p117 | 65 | CAC | Gln |
| p136 | 71 | CAC | His |
| p139 | 62 | CTC | Leu |
| p145 | 87 | AAC | Lys |
| p148 | 76 | TTC | Phe |
| p156 | 83 | CCC | Pro |
| p181 | 89 | TCC | Ser |
| p186 | 69 | ACG | Thr |
| p193 | 73 | TAC | Tyr |

As is clear from Table 4, when the amino acid at position 93 of the β subunit was substituted with another amino acid, heat resistance was improved again.

Example 5

Random mutation was introduced into the amino acid at position 167 of the β subunit.

The same operations described in Example 4 were carried out with the only exception that two types of primers used for introduction of a mutation were changed. The underlined portions indicate sites into which a mutation was to be introduced. The results are shown in Table 5.

β167RM-F:
(SEQ ID NO: 13)
gtgcccgaaatatgtgcggNNSaagatcggggaaatcgtcg

β167RM-R:
(SEQ ID NO: 14)
cgacgatttccccgatcttSNNccgcacatatttcgggcac

N: A + T + G + C  S: G + C

TABLE 5

Relative remaining activities of amino acid substitution products

| Name of plasmid | Relative remaining activities (%) | Nucleotide sequence | Amino acid |
|---|---|---|---|
| pJH601 | 40 | AAC | Asn |
| p52 | 70 | AGC | Ser |
| p209 | 71 | GGG | Gly |
| p212 | 65 | ATC | Ile |
| p230 | 77 | AAG | Lys |
| p236 | 56 | TGG | Trp |
| p238 | 66 | TAC | Tyr |
| p243 | 62 | GTG | Val |
| p251 | 75 | CCG | Pro |
| p266 | 53 | GCC | Ala |
| p278 | 60 | TGC | Cys |
| p283 | 61 | ACG | Thr |

As is clear from Table 5, when the amino acid at position 167 of the β subunit was substituted with another amino acid, heat resistance was improved again.

Example 6

Introduction of Mutation into Nitrile Hydratase Derived from *Rhodococcus rhodochrous* M8 Strain (1) Cloning of Nitrile Hydratase Gene The *Rhodococcus rhodochrous* M8 strain was cultured by the same method as that described in Example 1, and chromosomal DNA was then prepared from the cultured cell mass. Subsequently, PCR was carried out under the following conditions to amplify the nitrile hydratase gene thereof. It is to be noted that the *Rhodococcus rhodochrous* M8 strain can easily be obtained from Institute of Biochemistry and Physiology of Microorganisms of the Russian Academy of Sciences IBFM (VKPM S-926).

<Composition of reaction solution>

| | |
|---|---|
| Template DNA (chromosomal DNA) | 1 µl |
| 10× ExTaq Buffer (manufactured by Takara Shuzo) | 10 µl |
| Primer MH-01 | 1 µl |
| Primer MH-02 | 1 µl |
| 5 mM dNTPmix | 8 µl |
| Sterilized water | 78 µl |
| ExTaq DNA polymerase (manufactured by Takara Shuzo) | 1 µl |

<Primers>

(SEQ ID NO: 15)
MH-01: ccatggatggtatccacgacacaggcggcatgacc (SEQ ID NO: 16)
MH-02: aagcttcacgctggcctcgagcgcctttgtccag PCR was carried out by performing 30 cycles of (94° C., 30 seconds; 65° C., 30 seconds; and 72° C., 3 minutes) using Thermalcycler personal (Takara Shuzo).

Figure 3:
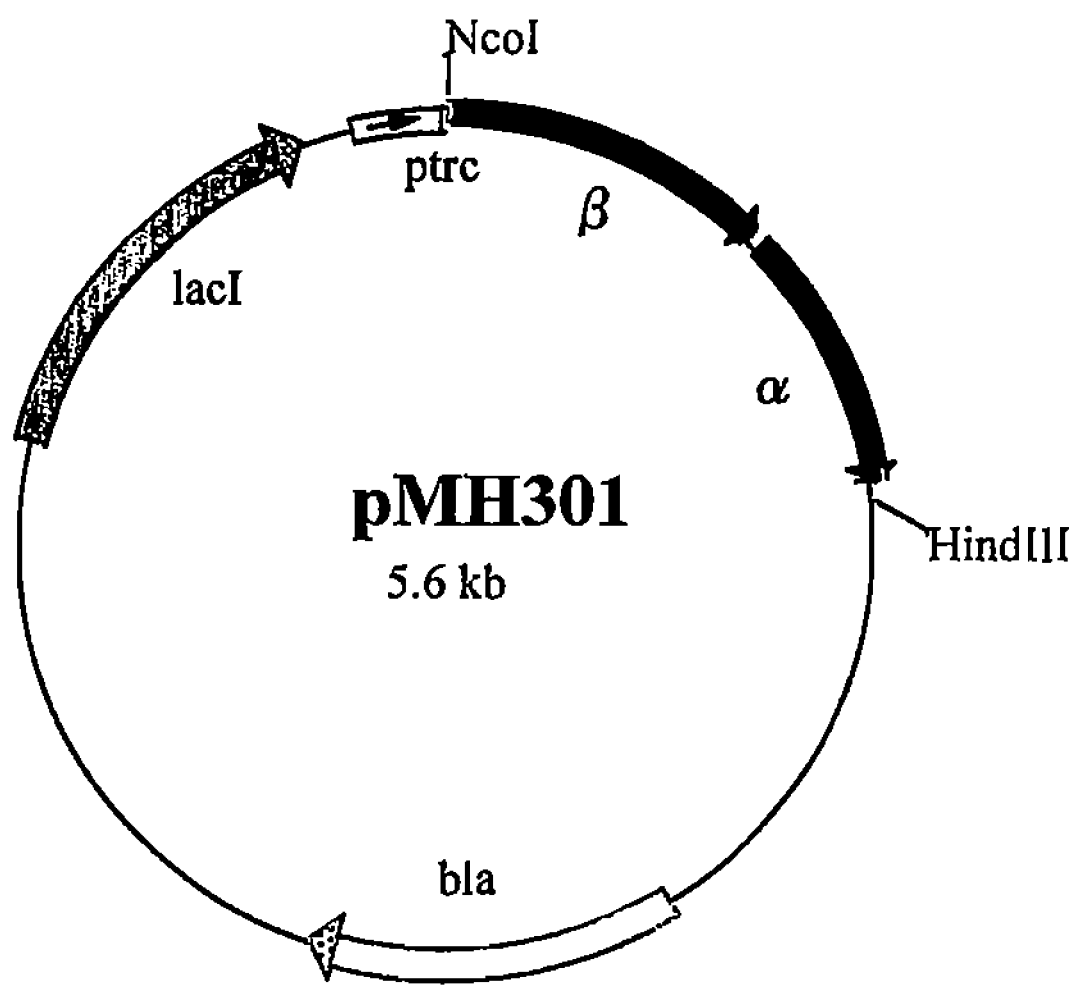
FIG. 3 is a structural view of the plasmid pMH301.

After completion of the PCR, 5 µl of the reaction solution was subjected to 0.7% agarose gel electrophoresis, and a 1.5 kb amplified fragment (SEQ ID NO: 17) was detected. After completion of the reaction, the obtained reaction solution was purified by GFX column (Amersham Biosciences), followed by cleavage with the restriction enzymes NcoI and HindIII. The PCR product that had been treated with the restriction enzymes was subjected to 0.7% agarose gel electrophoresis to recover a band around 1.5 kb. The recovered PCR product was ligated to a vector (the NcoI-HindIII site of pTrc99A) using Ligation Kit (Takara Shuzo), and JM109 was then transformed therewith. Several clones from the obtained transformant colony were inoculated into 1.5 ml of LB-Amp medium, and the medium was then subjected to shaking culture at 37° C. for 12 hours. After completion of the culture, the culture was subjected to centrifugation to collect cells. Thereafter, plasmid DNA was extracted from the collected cells, using Flexi Prep (manufactured by Amersham Biosciences). The obtained plasmid DNA was cleaved with the restriction enzymes NcoI and HindIII, and the cleaved DNA portion was then subjected to 0.7% agarose gel electrophoresis. Thereafter, a clone, to which a nitrile hydratase gene fragment (1.5 kb) was properly ligated, was selected. The selected clone was named as pMH301 (FIG. 3). JM109 was transformed with the pMH301 (JM109/pMH301).

(2) Site-Directed Mutagenesis

Site-directed mutagenesis was carried out according to the method described in Example 3, so that a mutation was introduced into the amino acid at position 93 of the β subunit. The underlined portion of the nucleotide sequence of a primer indicates the site into which a mutation was to be introduced.

(SEQ ID NO: 9)
NHM-F: gatcatcaccgaagaagggcgaaagcaccgtgtgc (SEQ ID NO: 10)
NHM-R: gcacacggtgctttcgcccttcttcggtgatgatc PCR was carried out under the following conditions using GeneAmp9700 (PE Bioscience). A reaction, which consisted of 95° C., 1 minute and 18 cycles of (95° C., 50 seconds; 60° C., 50 seconds; and 68° C., 14 minutes), and 68° C., 7 minutes, was carried out.

<Composition of reaction solution>

| | |
|---|---|
| pMH301 (10 ng) | 2 µl |
| 10× reaction buffer | 5 µl |
| Primer NHM-F (100 ng/µl) | 1 µl |
| Primer NHM-R (100 ng/µl) | 1 µl |
| 2.5 mM dNTPmix | 1 µl |
| Sterilized water | 36 µl |
| QuickSolution | 3 µl |
| Pfu Turbo DNA Polymerase | 1 µl |

After completion of the PCR, 10 µl of the reaction solution was subjected to 0.7% agarose gel electrophoresis, and an approximately 5 kb amplified fragment was detected. After confirmation of the presence of the amplified fragment, 1 µl of DpnI (included with the kit) was added to the PCR reaction solution. Thereafter, a reaction was carried out at 37° C. for 1 hour, and template DNA was eliminated. Subsequently, transformation was carried out using XL10-GOLD ultracompetent cell (included with the kit). 2 µl of the DpnI-treated PCR reaction solution was mixed with 45 µl of competent cells, and the obtained mixture was then incubated at 4° C. for 30 minutes, followed by performing heat shock at 42° C. for 30 seconds. Thereafter, 0.5 ml of NZY+ medium (1% NZ amine, 0.5% yeast extract, 0.5% NaCl, 12.5 mM MgCl$_2$, 12.5 mM MgSO$_4$, 0.4% glucose, pH 7.5) was added to the reaction product, and the obtained mixture was further cultured at 37° C. for 1 hour. 250 µl of the obtained culture solution was plated on an LB plate (1% NaCl, 1% trypton, 0.5% yeast extract, 2% agar, 50 mg/l ampicillin), and it was then cultured at 37° C. for 1 day.

Several colonies obtained as above were cultured in LB medium (50 mg/l ampicillin), and a plasmid was then prepared using FlexiPrep Kit (Amersham Biosciences). Finally, the nucleotide sequence of the obtained plasmid was determined, and thus it was confirmed that a mutation of interest had been introduced. Thus, pMH404, a plasmid introduced a mutation of Eβ93G, was obtained.

Likewise, a mutation was also introduced into the amino acid at position 167 of the β subunit, using the following primers. The underlined portions indicate sites into which a mutation was to be introduced.

(SEQ ID NO: 18)
β167-F: cccgaaatatgtgcggagcaagatcggggaaatcg (SEQ ID NO: 19)
β167-R: cgatttcccccgatcttgctccgcacatatttcggg Several colonies obtained as above were cultured in LB medium (50 mg/l ampicillin), and a plasmid was then extracted. The nucleotide sequence of the obtained plasmid was determined, and thus it was confirmed that a mutation of interest had been introduced. Thus, pMH508, a plasmid introduced a mutation of Nβ167S, was obtained.

(3) Activity Measurement

XL10/pMH404XL10-Gold/pMH508 obtained in process (2) and XL10/pMH301 were inoculated into 10 ml of LB-Amp medium (containing 1 mM IPTG and 5 μg/ml CoCl$_2$), followed by liquid culture at 37° C. for 12 hours. The obtained culture was subjected to a heat treatment at a temperature of 55° C. for 30 minutes. Thereafter, the remaining activity of the nitrile hydratase was measured.

Activity measurement was carried out by the same method as described in Example 1(4). The cell, which had not been subjected to a heat treatment and had been kept cold at 4° C., was defined as an untreated cell, and it was used as a control for comparison. The remaining activities of such cells were obtained. The results are shown in Table 6.

TABLE 6

| Name of plasmid | Remaining activity (%) | Mutated site |
|---|---|---|
| pMH301 | 45 | None |
| pMH404 | 80 | Eβ93G |
| pMH508 | 76 | Nβ167S |

As is clear from Table 6, it was found that heat resistance was improved by introduction of Eβ93G and Nβ167S, even in a nitrile hydratase derived from the *Rhodococcus rhodochrous* M8 strain.

Example 7

Obtainment of Improved Nitrile Hydratase Gene (II)

(1) Construction of Mutant Gene Library

Figure 4:
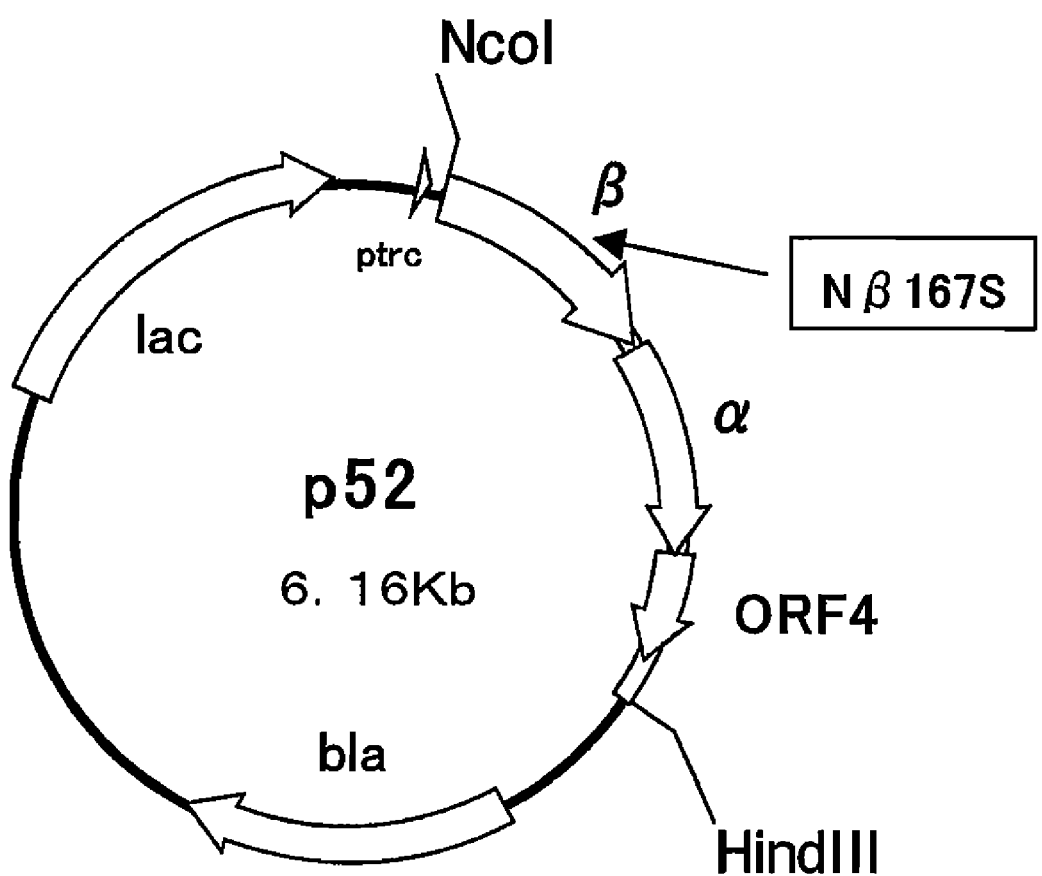
FIG. 4 is a structural view of the plasmid p52.

In the present example, random mutagenesis was carried out on a nitrile hydratase gene derived from the *Rhodococcus rhodochrous* J-1 strain. For the mutagenesis, a nucleotide substitution due to incorrect incorporation of nucleotides by PCR was utilized. As a plasmid used as a template, the plasmid p52, wherein asparagine, the amino acid at position 167 of the β subunit of a wild-type strain, had been substituted with serine, was used (FIG. 4).

PCR for random mutagenesis into such a nitrile hydratase gene was carried out using a reaction solution having the following composition under the following reaction conditions.

| <Composition of reaction solution> | |
|---|---|
| Template plasmid (p52) (10 ng) | 1 μl |
| 10× PCR buffer (manufactured by GIBCO) | 10 μl |
| 50 mM MgCl$_2$ (manufactured by GIBCO) | 3 μl |
| Primer Trc-02 (100 ng/μl) | 1 μl |
| Primer Trc-03 (100 ng/μl) | 1 μl |
| 2.5 mM dNTPmix | 8 μl |
| 10 mM dITP | 2 μl |
| 10 mM dBraUTP | 2 μl |
| Sterilized water | 71 μl |
| Taq DNA polymerase (manufactured by GIBCO) | 1 μl |

```
<Primers>
TRC-02:
ggaattcgtataatgtgtggaattgtgagc        (SEQ ID NO: 7)

TRC-03:
ggctgaaaatcttctctcatccgcc             (SEQ ID NO: 8)
```

PCR was carried out by performing 30 cycles of (94° C., 30 seconds; 65° C., 30 seconds; and 72° C., 3 minutes) using GeneAmp9700 (PE Bioscience).

After completion of the PCR, 5 μl of the reaction solution was subjected to 0.7% agarose gel electrophoresis, and a 3 kb amplified fragment was detected. After completion of the reaction, the obtained reaction solution was purified by GFX column (Amersham Biosciences), followed by cleavage with the restriction enzymes NcoI and HindIII. The PCR product that had been treated with the restriction enzymes was subjected to 0.7% agarose gel electrophoresis to recover a band around 3 kb. The recovered PCR product was ligated to a vector (the NcoI-HindIII site of pTrc99A) using Ligation Kit (Takara Shuzo), and JM109 was then transformed with this ligated product.

(2) Screening of Heat-Resistant Nitrile Hydratase and Identification of Mutated Site The JM109 transformant comprising a mutant nitrile hydratase gene obtained in the aforementioned process (1) and JM109/pJH601 used as a wild-type nitrile hydratase-generating strain were used to measure the remaining activity of the nitrile hydratase.

Heat resistance was evaluated by the same method described in Example 1(4) with the only exception that the treating temperature was changed to 60° C. for 20 minutes.

As a result of screening that was performed on several thousands of recombinants each having a randomly mutated nitrile hydratase gene, recombinants that exhibited a remaining activity that was higher than that of a wild-type nitrile hydratase were selected. The results regarding such remaining activity are shown in Table 7.

TABLE 7

| Name of plasmid | Remaining activity (%) | Mutated site |
|---|---|---|
| pJH601 | 10 | None |
| p52 | 25 | Nβ167S |
| pA077 | 51 | (Nβ167S, Lβ144H, Vβ219A, Vα129A, Lα196P) |

The above recombinants were cultured, and a plasmid was then recovered. The recovered plasmid was named as plasmid pA077. The nucleotide sequence of the plasmid pA077 was determined. BeckmanCEQ-2000XL was used to determine the nucleotide sequence. The amino acid sequence encoded by the mutant gene sequence of the plasmid pA077 was mutated at 5 sites, Nβ167S, Lβ144H, Vβ219A, Vα129A, and Lα196P.

Example 8

Preparation and Evaluation of Recombinant *Escherichia coli*

(1) Construction of Plasmid

A mutation was introduced into the template plasmid p52 (FIG. 4) based on the information regarding the mutated sites obtained in Example 7(2). Site-directed mutagenesis was applied to introduce a mutation, and a commercially available kit, QuikChange XL Site-Directed Mutagenesis Kit (Stratagene), was used. The experiment was carried out in accordance with an operation manual.

Two types of primers used for introduction of a mutation were synthesized. The underlined portion indicates a site, into which mutation was introduced.

```
β144-F:
ggagccgagtttctctcacggtgacaagatc    (SEQ ID NO: 20)

β144-R:
gatcttgtcaccgtgagagaaactcggctcc    (SEQ ID NO: 21)
```

In order to introduce a mutation, PCR was carried out under the following conditions using GeneAmp9700 (PE Bioscience). A reaction, which consisted of 95° C., 1 minute, 18 cycles of (95° C., 50 seconds; 60° C., 50 seconds; and 68° C., 14 minutes), and 68° C., 7 minutes, was carried out.

| <Composition of reaction solution> | |
|---|---|
| Template plasmid p52 (10 ng) | 2 µl |
| 10× reaction buffer | 5 µl |
| Primer β144-F (100 ng/µl) | 1 µl |
| Primer β144-R (100 ng/µl) | 1 µl |
| 2.5 mM dNTPmix | 1 µl |
| Sterilized water | 36 µl |
| QuickSolution | 3 µl |
| Pfu Turbo DNA Polymerase | 1 µl |

After completion of the PCR, 10 µl of the reaction solution was subjected to 0.7% agarose gel electrophoresis, and an approximately 11 kb amplified fragment was detected. After confirmation of the presence of the amplified fragment, 1 µl of DpnI (included with the kit) was added to the PCR reaction solution. Thereafter, a reaction was carried out at 37° C. for 1 hour, and the template plasmid was eliminated.

Subsequently, transformation was carried out using XL10-GOLD ultracompetent cell (included with the kit). 2 µl of the DpnI-treated PCR reaction solution was mixed with 45 µl of competent cells, and the obtained mixture was then incubated at 4° C. for 30 minutes, followed by performing heat shock at 42° C. for 30 seconds. Thereafter, 0.5 ml of NZY⁺ medium (1% NZ amine, 0.5% yeast extract, 0.5% NaCl, 12.5 mM MgCl$_2$, 12.5 mM MgSO$_4$, 0.4% glucose, pH 7.5) was added to the reaction product, and the obtained mixture was further cultured at 37° C. for 1 hour. 250 µl of the obtained culture solution was plated on an LB plate (1% NaCl, 1% trypton, 0.5% yeast extract, 2% agar, 50 mg/l ampicillin), and it was then cultured at 37° C. for 1 day.

Several colonies obtained as above were cultured in 1.5 ml of LB medium (50 mg/l ampicillin), and a plasmid was then prepared using FlexiPrep Kit (Amersham Biosciences). Finally, the nucleotide sequence of the obtained plasmid was determined, and thus it was confirmed that a mutation of interest had been introduced. Thus, pAB001, a plasmid introduced a mutation of Lβ144H, was obtained.

Subsequently, a mutation of Vβ219A or Vα129A was introduced by the same means as described above using p52 or pAB001 as a template plasmid. The following primers were used.

```
β219-F:
gaaagacgtagtgtgcgccgatctctgggaacc    (SEQ ID NO: 22)

β219-R:
ggttcccagagatcggcgcacactacgtctttc    (SEQ ID NO: 23)

α129-F:
gagtaccggtcccgagcggtagcggaccctcg     (SEQ ID NO: 24)

α129-R:
cgagggtccgctaccgctcgggaccggtactc     (SEQ ID NO: 25)
```

The obtained plasmids were named as pAB002 (Nβ167S, Vβ219A), pAB003 (Nβ167S, Vα129A), and pAB004 (Nβ167S, Lβ144H, Vβ219A).

(2) Evaluation of Heat Resistance

*Escherichia coli* JM109 was transformed with the plasmid comprising a mutant nitrile hydratase gene obtained in (1) above to obtain a recombinant strain. This recombinant strain was inoculated into 1.5 ml of LB-Amp medium (containing 1 mM IPTG and 5 µg/ml CoCl$_2$), followed by liquid culture at 37° C. for 12 hours. The obtained culture solution was subjected to a heat treatment at a temperature of 60° C. for 20 minutes. Thereafter, the remaining activity of the nitrile hydratase was measured. Activity measurement was carried out by the same method as described in Example 1(4). The results regarding such remaining activity are shown in Table 8.

TABLE 8

| Name of plasmid | Remaining activity (%) | Mutated site |
|---|---|---|
| pJH601 | 10 | None |
| p52 | 25 | Nβ167S |
| pAB001 | 36 | (Nβ167S, Lβ144H) |
| pAB002 | 32 | (Nβ167S, Vβ219A) |
| pAB003 | 60 | (Nβ167S, Vα129A) |
| pAB004 | 55 | (Nβ167S, Lβ144H, Vβ219A) |

As is clear from Table 8, it was revealed that heat resistance was improved by introduction of Lβ144H, Vβ219A, and Vβ219A.

Example 9

Preparation and Evaluation of Recombinant *Rhodococcus* Strain (1) Construction of Plasmid A plasmid used for a *Rhodococcus* strain having a mutation (Nβ167S) at position 167 of the β subunit was prepared by the following method. For introduction of a mutation, site-directed mutagenesis was applied, and a commercially available kit, QuikChange XL Site-Directed Mutagenesis Kit (Stratagene) was used. The experiment was carried out in accordance with an operation manual. As a template plasmid into which a mutation be introduced, pSJ034 was used.

Two types of primers used to introduce a mutation were synthesized. The underlined portion indicates a site, into which a mutation was introduced.

```
                                               (SEQ ID NO: 18)
β167-F:  cccgaaatatgtgcggagcaagatcggggaaatcg (SEQ ID NO: 19)
β167-R:  cgatttccccgatcttgctccgcacatatttcggg
```

PCR for introduction of a mutation was carried out under the same conditions as those described in Example 3(1).

<Composition of reaction solution>

| | |
|---|---|
| Template plasmid pSJ034 (10 ng) | 2 µl |
| 10× reaction buffer | 5 µl |
| Primer β167-F (100 ng/µl) | 1 µl |
| Primer β167-R (100 ng/µl) | 1 µl |
| 2.5 mM dNTPmix | 1 µl |
| Sterilized water | 36 µl |
| QuickSolution | 3 µl |
| Pfu Turbo DNA Polymerase | 1 µl |

After completion of the PCR, p52R, a plasmid used to introduce a mutation of Nβ167S into a *Rhodococcus* strain, was obtained by the same means as described in Example 3(1).

Subsequently, a mutation of Lβ144H, Vβ219A, or Vα129A was introduced by the same means as described above, using p52R as a template plasmid. The following primers were used.

```
β144-F:
ggagccgagtttctctcacggtgacaagatc      (SEQ ID NO: 20)

β144-R:
gatcttgtcaccgtgagagaaactcggctcc      (SEQ ID NO: 21)

β219-F:
gaaagacgtagtgtgcgccgatctctgggaacc    (SEQ ID NO: 22)

β219-R:
ggttcccagagatcggcgcacactacgtctttc    (SEQ ID NO: 23)

α129-F:
gagtaccggtcccgagcggtagcggaccctcg     (SEQ ID NO: 24)

α129-R:
cgagggtccgctaccgctcgggaccggtactc     (SEQ ID NO: 25)
```

The obtained plasmids were named as pAR001 (Nβ167S, Lβ144H), pAR002 (Nβ167S, Vβ219A), and pAR003 (Nβ167S, Vα129A). Furthermore, using the obtained plasmid pAR001 as a template plasmid, a mutation of Vβ219A was introduced by the same above means. The obtained plasmid was named as pAR004 (Nβ167S, Lβ144H, Vβ219A).

(2) Production of Recombinant *Rhodococcus* Strain

The cells of *Rhodococcus rhodochrous* ATCC 12674 strain that were at the logarithmic growth phase were collected using a centrifugal separator. The cells were washed three times with ice-cold sterilized water, and were then suspended in sterilized water. 1 µl of the plasmid prepared in (1) above was mixed with 10 µl of the cell mass suspension, and the obtained mixture was then cooled on ice.

Thereafter, the same operations as those described in Example 3(2) were conducted.

(3) Evaluation of Heat Resistance of Recombinant *Rhodococcus* Strain

Using the obtained recombinant *Rhodococcus* strain, the remaining nitrile hydratase activity thereof after a heat treatment was examined by the same method as that described in Example 3(3).

Each of the recombinant bacteria of genus *Rhodococcus* was inoculated into MYK medium (containing 50 µg/ml kanamycin, 5 µg/ml CoCl$_2$, and 0.1% urea), and it was then subjected to shaking culture at 30° C. for 3 days. Thereafter, cells were collected by centrifugation, and the cell mass was washed with a 100 mM phosphate buffer solution (pH 8.0). Finally, it was suspended in a small amount of buffer solution.

As a heat treatment, 0.5 ml of a cell mass suspension that had been appropriately diluted was placed in a test tube, and it was incubated in a water bath at a temperature of 65° C. for 30 minutes. Thereafter, it was cooled on ice.

Activity measurement was carried out by the same method as that described in Example 3(3). The results regarding such remaining activity are shown in Table 9.

TABLE 9

| Name of plasmid | Remaining activity (%) | Mutated site |
|---|---|---|
| pSJ034 | 31 | None |
| p52R | 69 | Nβ167S |
| pAR001 | 66 | (Nβ167S, Lβ144H) |
| pAR002 | 72 | (Nβ167S, Vβ219A) |
| pAR003 | 74 | (Nβ167S, Vα129A) |
| pAR004 | 69 | (Nβ167S, Lβ144H, Vβ219A) |

ATCC12674/pSJ034 had a remaining activity of 31% after a heat treatment at 65° C. for 30 minutes. In contrast, ATCC 12674/pAR001 to pAR004 had a remaining activity of 60% or more. Thus, it was confirmed that the heat resistance of the improved nitrile hydratase was improved.

(3) Evaluation of Acrylamide Resistance

Using the transformant used in Example 9(2), acrylamide resistance was evaluated. A reaction solution having the following composition was prepared, and it was stirred at 30° C. for reaction. The cell amount of each cell mass suspension used for the reaction was adjusted in accordance with the measurement results of the activity measured by the method described in Example 3(3), such that the enzyme activity unit (U) amount could be equally obtained. As a control for comparison, ATCC12674/pSJ034 having a wild-type nitrile hydratase was used.

<Composition of reaction solution>

| | |
|---|---|
| 30% acrylamide solution | 95 g |
| Acrylonitrile | 3 g |
| 1M phosphate buffer | 1 g |
| Conserved cell solution (the equal enzyme activity unit (U) amount) | 1 g |

1 ml of the reaction solution was sampled before initiation of the reaction (0-hour), 0.5 hours after the reaction, and 20 hours after the reaction. It was filtrated using a 0.22 µm filter. The obtained filtrate was subjected to gas chromatography for analysis (analytical device: gas chromatograph GC-14B (manufactured by Shimadzu Corporation); detector: FID; detection temperature: 200° C.; column: 1.1 m packed glass column filled with Porapak PS (column filler manufactured by Waters); column temperature: 190° C.; carrier gas: N2).

The ratio (%) of acrylonitrile remaining in the filtrate, which was obtained as a result of the analysis, is shown in Table 10.

TABLE 10

Remaining acrylonitrile (%)

| Name of plasmid | Mutated site | Remaining acrylonitrile amount (%) 0-hour | 0.5-hour | 20-hour | AN consumption (%) |
|---|---|---|---|---|---|
| pSJ034 | None | 3.12 | 2.81 | 1.98 | 1.14 |
| p52R | β167 | 3.12 | 2.83 | 1.80 | 1.32 |
| pAR001 | β167 + β144 | 3.12 | 2.75 | 1.54 | 1.58 |
| pAR002 | β167 + β219 | 3.12 | 2.81 | 1.25 | 1.87 |
| pAR003 | β167 + α129 | 3.12 | 2.75 | 0.94 | 2.18 |
| pAR004 | β167 + β144 + β219 + α129 + α196 | 3.12 | 2.75 | 0.01 | 3.11 |

As stated above, from the fact that the improved nitrile hydratase consumed a higher amount of acrylonitrile than pSJ034 used as a control for comparison did, it was found that the improved nitrile hydratase maintains its activity in the presence of a high concentration of acrylamide, and that it has high resistance to acrylamide.

Example 10

Introduction of Mutation into Nitrile Hydratase Derived from *Rhodococcus rhodochrous* M8 Strain, Production of Recombinant, and Evaluation Thereof (1) Production of Mutation-Introduced Mutant A mutation was introduced into a nitrile hydratase derived from the *Rhodococcus rhodochrous* M8 strain. Site-directed mutagenesis was carried out by the same method as that described in Example 6(2) with the exception that pMH301 (FIG. 3), an expression plasmid comprising a gene (SEQ ID NO: 17) encoding a nitrile hydratase derived from the *Rhodococcus rhodochrous* M8 strain, was used as a plasmid. The obtained plasmids were named as pMH508 (β167S), pMH601 (Nβ167S, Lβ144H), pMH602 (Nβ167S, Vβ219A), and pMH603 (Nβ167S, Vα129A).

JM109 was transformed with the above plasmid to produce a mutation-introduced recombinant strain. The obtained recombinant strain was inoculated into 10 ml of LB-Amp medium (containing 1 mM IPTG and 5 μg/ml CoCl$_2$), followed by liquid culture at 37° C. for 12 hours.

(2) Evaluation of Heat Resistance

The obtained culture was subjected to a heat treatment at a temperature of 60° C. for 20 minutes, and the remaining activity of the nitrile hydratase was measured. Activity measurement was carried out by the same method as that described in Example 7(2). A culture, which had not been subjected to a heat treatment and had been kept cold at 4° C., was defined as an untreated cell strain, and it was used as a control for comparison. The remaining activities of such strains were obtained. The results regarding such remaining activity are shown in Table 11.

TABLE 11

| Name of plasmid | Remaining activity (%) | Mutated site |
|---|---|---|
| pMH301 | 10 | None |
| pMH508 | 21 | Nβ167S |
| pMH601 | 42 | (Nβ167S, Lβ144H) |
| pMH602 | 38 | (Nβ167S, Vβ219A) |
| pMH603 | 33 | (Nβ167S, Vα129A) |

It was shown that an improved nitrile hydratase had an improved heat resistance even in the case of the *Rhodococcus rhodochrous* M8 strain.

Example 11

Obtainment of Mutant Nitrile Hydratase Gene (1) Construction of Plasmid

A nitrile hydratase gene, into which a random mutation was introduced by the same method as that described in Example 1(3) using the pJH601 produced in Example 1, was amplified, and thereafter, a 3 kb PCR product was recovered.

The recovered PCR product was inserted into the NcoI-HindIII site of a plasmid pFY529 using Ligation Kit (Takara Shuzo), and JM109 was then transformed therewith to obtain a transformant. It is to be noted that production of pFY529 is described in Reference example 1.

(2) Obtainment of Substrate-Specific Mutant Nitrile Hydratase and Identification of Mutated Site The JM109 transformant comprising a mutant nitrile hydratase gene obtained in the aforementioned process (1) and JM109/pJH601 were used to measure a nitrile hydratase activity in the same manner as that described in Example 1(4).

As a result of screening performed on several hundreds of transformants, one type of strain (JM109/pNHM101), which exhibited significantly a high activity to 3-cyanopyridine when compared with a wild-type strain, was obtained. That cell strain was cultured, a plasmid was then recovered, and the nucleotide sequence thereof was determined. Beckman CEQ-2000XL was used to determine the nucleotide sequence. In the nitrile hydratase gene of the present plasmid, the tryptophan residue (TGG) at position 48 of the β subunit was substituted with an arginine residue (CGG).

Example 12

Production of Recombinant *Rhodococcus* Strain

The properties of the mutant enzyme obtained in Example 11 were confirmed using a recombinant *Rhodococcus* strain.

(1) Construction of Plasmid Used for Introduction into *Rhodococcus* Strain

A plasmid having a mutation of pNHM11 (Wβ48R), which is used for introduction into a *Rhodococcus* strain, was produced by the following method. Such a mutation was introduced by the method according to Kurosawa et al. (Gene. 1991 15; 102: 67-70). As a plasmid into which such a mutation be introduced, pSJ034 was used. Such pSJ034 is a plasmid that allows nitrile hydratase to express in a *Rhodococcus* strain. The plasmid pSJ034 was produced from pSJ023 by the method described in Japanese Patent Application Laid-Open No. 10-337185. It is to be noted that pSJ023 was deposited as a transformant "*R. rhodochrous* ATCC12674/pSJ023" with International Patent Organism Depositary, National Institute of Advanced Industrial Science and Technology, Independent Administrative Institution (at Tsukuba Central 6, 1-1-1 Higashi, Tsukuba, Ibaraki, Japan) under accession No. FERM BP-6232.

$1^{st}$ PCR

Two types of $1^{st}$ PCR reactions were carried out under the following conditions. Using GeneAmp9700 (PE Bioscience), a reaction, which consisted of 95° C., 1 minute, 30 cycles of (95° C., 60 seconds; 60° C., 60 seconds; and 72° C., 10 minutes), and 72° C., 7 minutes, was carried out.

<Composition of reaction solution>

| | |
|---|---|
| pSJ034 (10 ng) | 2 µl |
| 10× reaction buffer | 5 µl |
| Primer 1 (100 ng/µl) | 1 µl |
| Primer 2 (100 ng/µl) | 1 µl |
| 2.5 mM dNTPmix | 1 µl |
| Sterilized water | 36 µl |
| Pfu Turbo DNA Polymerase | 1 µl |

Such two types of PCR reactions were carried out by the combined use of primer 1 (NR-01) with primer 2 (NH18), and by the combined use of primer 1 (NOXbaI-1) with primer 2 (RE1-02).

```
NR-01:
AACGTCGACACCGGTGGTGG            (SEQ ID NO: 26)

NH18:
CCGCGACTTGTCCCGCCACGATATGCCC    (SEQ ID NO: 27)
```

(Primers used for introduction of mutation; the underlined portion indicates a site to be mutated.)

```
NOXbaI-1:   GTACCCGGGGATCCACTAGA   (SEQ ID NO: 28)

RE1-02:     CCTTAGTCAGCTTCTGTCCG   (SEQ ID NO: 29)
```

After completion of the PCR, 1 µl of the reaction solution was subjected to 0.7% agarose gel electrophoresis to confirm the presence of an amplified fragment. Thereafter, the remaining reaction solution was subjected to agarose gel electrophoresis under the same conditions to purify the amplified fragment. $2^{nd}$ PCR Using the two types of PCR fragments obtained in the $1^{st}$ PCR, $2^{nd}$ PCR was carried out under the following conditions.

<Composition of reaction solution>

| | |
|---|---|
| 10× reaction buffer | 5 µl |
| 1st PCR fragment 1 | 1 µl |
| 1st PCR fragment 2 | 1 µl |
| 2.5 mM dNTPmix | 1 µl |
| Sterilized water | 36 µl |
| Pfu Turbo DNA Polymerase | 1 µl |

The reaction solution was treated at 93° C. for 10 minutes under conditions wherein no enzymes were added. Thereafter, the resultant was cooled to 37° C. over 1 hour, and it was then left at 37° C. for 15 minutes. Thereafter, an enzyme was added to the resultant, and a reaction consisting of 1 minute, 30 cycles of (95° C., 60 seconds; 60° C., 60 seconds; and 72° C., 10 minutes), and 72° C., 7 minutes, was carried out.

The obtained PCR product was confirmed by agarose gel electrophoresis, and was then treated with XbaI and Sse8387I. Thereafter, a DNA fragment was purified by agarose gel electrophoresis.

The purified PCR fragment was ligated to a vector pSJ034 (XbaI-Sse8387I site) using Ligation Kit (Takara Shuzo), and JM109 was then transformed therewith. Several clones from the obtained transformant colony were inoculated into 1.5 ml of LB-Amp medium, and the medium was then subjected to shaking culture at 37° C. for 12 hours. After completion of the culture, the culture was collected by centrifugation, and plasmid DNA was then extracted using Flexi Prep (manufactured by Amersham Biosciences). The obtained plasmid DNA was cleaved with the restriction enzymes XbaI and Sse8387I, and the cleaved DNA portion was then subjected to 0.7% agarose gel electrophoresis. Thereafter, a clone, to which a nitrile hydratase gene fragment (approximately 2 kb) was properly ligated, was selected. Finally, the nucleotide sequence of the obtained plasmid was determined, and thus it was confirmed that a mutation of interest had been introduced. Thus, pAJ001, a plasmid introduced a mutation of Wβ48R, was obtained.

(2) Obtainment of Recombinant *Rhodococcus* Strain into which Mutant Enzyme Gene Had been Introduced The cells of *Rhodococcus rhodochrous* ATCC 12674 strain that were at the logarithmic growth phase were collected using a centrifugal separator, and they were then washed three times with ice-cold sterilized water. Thereafter, the cells were suspended in sterilized water.

1 µl of the plasmid pAJ001 prepared in (1) above was mixed with 10 µl of the cell mass suspension, and the mixture was then cooled on ice.

Thereafter, the same treatment as that performed in Example 3(2) was carried out to obtain a recombinant *Rhodococcus* strain.

(3) Activity of Recombinant *Rhodococcus* Strain

The activity of the obtained recombinant *Rhodococcus* strain to acrylamide and 3-cyanopyridine was examined. The obtained recombinant *Rhodococcus* strain was inoculated into a 96-well deep well plate, in which 1 ml of LB-Amp medium (containing 1 mM IPTG and 5 µg/ml CoCl$_2$) had been placed, and it was then subjected to liquid culture at 37° C. for 12 hours. Thereafter, the nitrile hydratase activity of the obtained culture was measured.

For activity measurement, a 5% acrylonitrile/50 mM phosphate buffer solution (pH 7.7) or a 0.5% 3-cyanopyridine/50 mM phosphate buffer solution (pH 7.7) was added to the cell solution in an amount equal thereto, and the reaction was then carried out at 30° C. for 30 minutes. After completion of the reaction, an equal amount of 0.1 M phosphoric acid was added to the reaction solution, and the obtained mixture was then centrifuged. The obtained supernatant was appropriately diluted, and the dilute solution was then subjected to HPLC. Thereafter, the concentration of the generated acrylamide was analyzed (acrylamide: WAKOSIL 5C8 (Wako Pure Chemical Industries, Ltd.) and 10% acetonitrile containing 5 mM phosphoric acid; nicotinamide: WAKOSIL 5C8 (Wako Pure Chemical Industries, Ltd.) and 35% acetonitrile containing 5 mM phosphoric acid).

As a control for comparison, ATCC12674/pSJ034 having a wild-type nitrile hydratase was prepared.

The results are shown in Table 12.

TABLE 12

| | Acrylamide | 3-cyanopyridine |
|---|---|---|
| ATCC12674/pSJ034 | 100 | 20 |
| ATCC12674/pAJ001 | 80 | 223 |

Example 13

A mutant nitrile hydratase gene library was produced in the same manner as described above using pNHM101 as a template, and screening was then performed using heat resistance as an indicator.

Such screening was performed under the same conditions by the same method as those described in Example 1(4).

As a result of the screening performed on several hundreds of transformant strains, one type of stain (JM109/pNHM111), which exhibited a remaining activity higher than that of a wild-type strain, was obtained. That cell strain was cultured, a plasmid was then recovered, and the nucleotide sequence thereof was determined. Beckman CEQ-2000XL was used to determine the nucleotide sequence. In the nitrile hydratase gene of the present plasmid, the histidine residue (CAC) at position 26 of the β subunit was substituted with an arginine residue (CGC), as well as a mutation of pNHM101.

Example 14

The properties of the mutation (Hβ26R) of the heat-resistant enzyme obtained in Example 13 were confirmed using a recombinant *Rhodococcus* strain.

Using NH-25 as a mutant primer instead of NH-18, a plasmid was produced in the same manner as described in Example 12. The produced plasmid was named as pAJ006, and it was introduced into the *Rhodococcus rhodochrous* ATCC12674 strain in the same manner as described in Example 12.

(SEQ ID NO: 30)
NH25: CCCTCCCACTCGTAGCGGAAGAAGGGCTCG (Primer used for introduction of mutation; the underlined portion indicates a site to be mutated.)

Using the obtained recombinant *Rhodococcus* strain, heat resistance was examined in the same manner as described in Example 3(3). As a control for comparison, ATCC12674/pSJ034 having a wild-type nitrile hydratase was prepared.

0.5 ml of the obtained cell mass suspension was placed in a test tube, and it was incubated in a water bath at each temperature of 65° C. and 70° C. for 10 minutes. Thereafter, it was cooled on ice. The remaining activity was evaluated as a relative activity based on the condition where the initial activity of a cell strain that had not been subjected to a heat treatment and had been kept cold at 4° C. (untreated stain) was defined as 100%.

After completion of the heat treatment at 70° C. for 10 minutes, ATCC12674/pSJ034 maintained a remaining activity of 4%. In contrast, ATCC 12674/pAJ006 maintained a remaining activity of 40%. Thus, it was revealed that the mutant enzyme (Hβ26R) had an improved heat resistance.

Reference Example 1

Production of Esterase Expression Plasmid pFY529

Figure 5A:
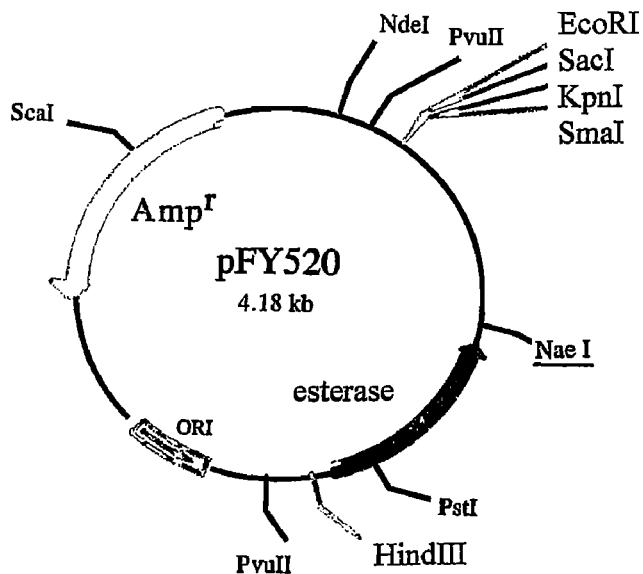
FIG. 5A is a structural view of the plasmid pCF002.
Figure 5A:
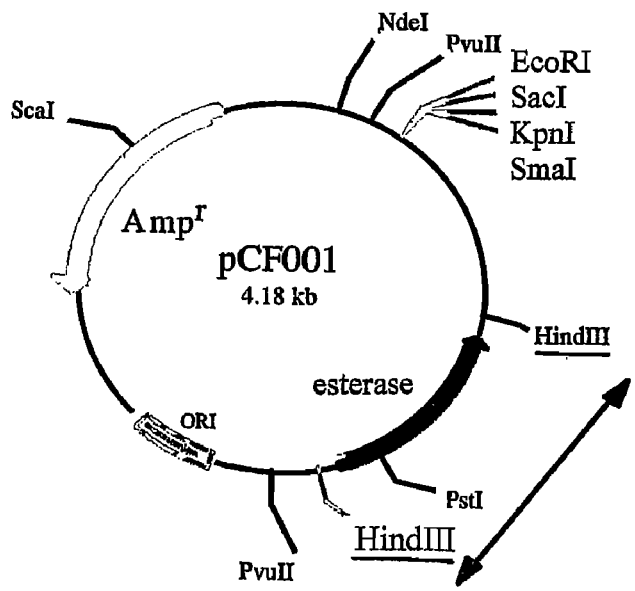
Figure 5A:
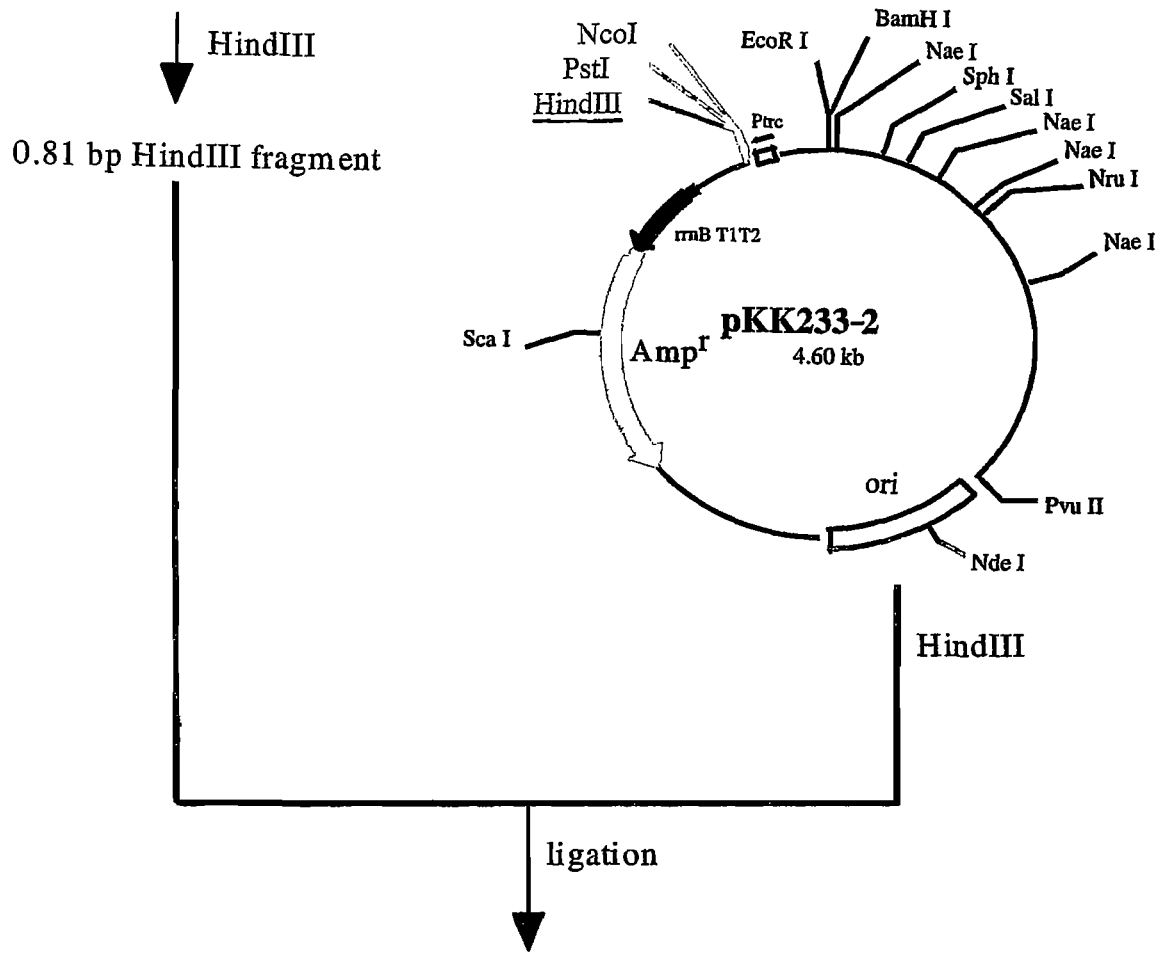
Figure 5A:
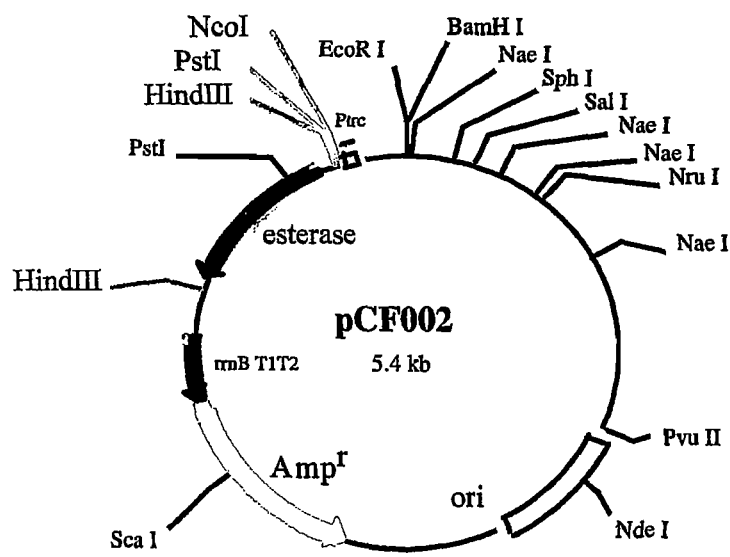
Figure 5B:
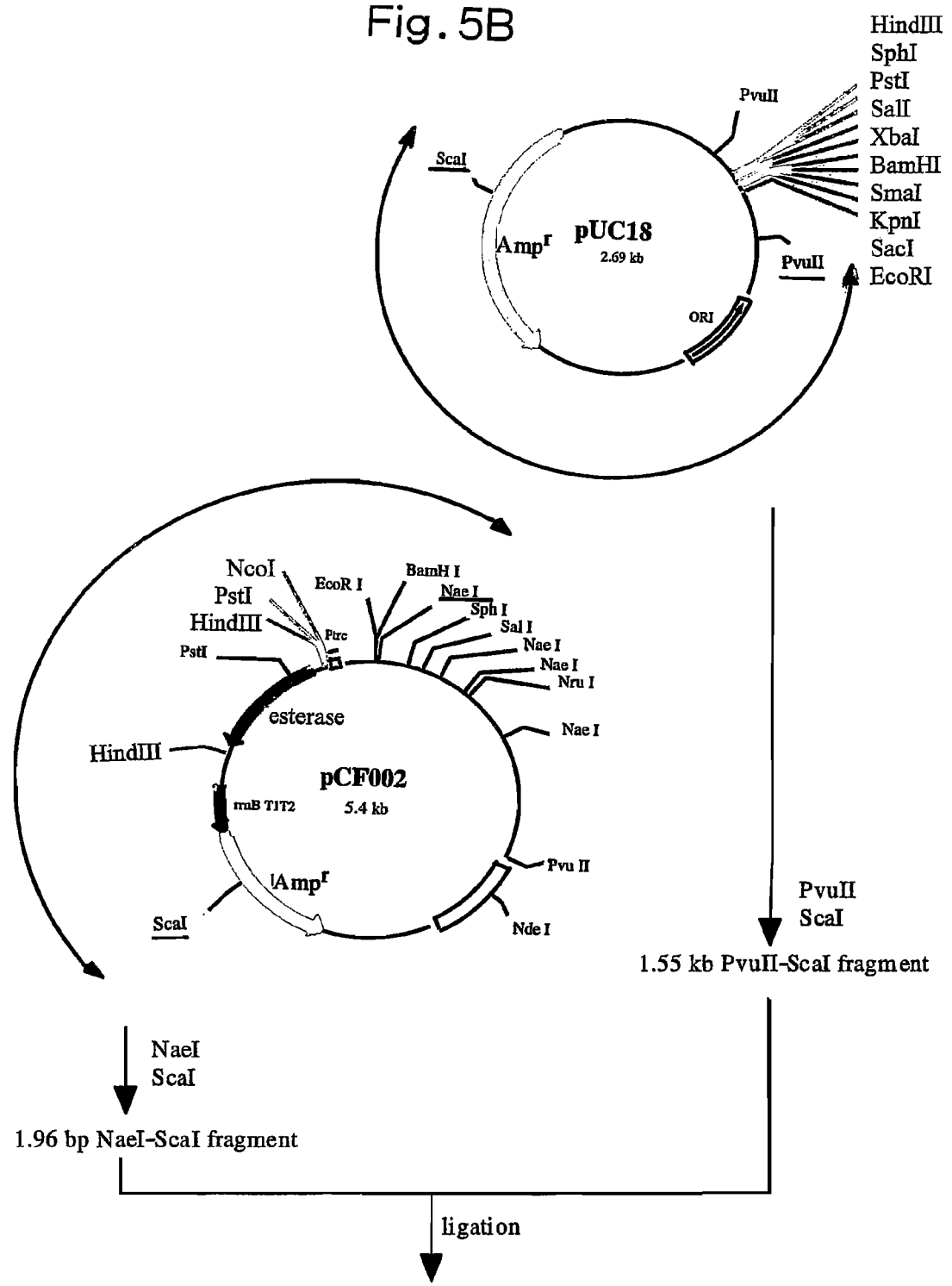
FIG. 5B is a structural view of the plasmid pFY529.
Figure 5B:
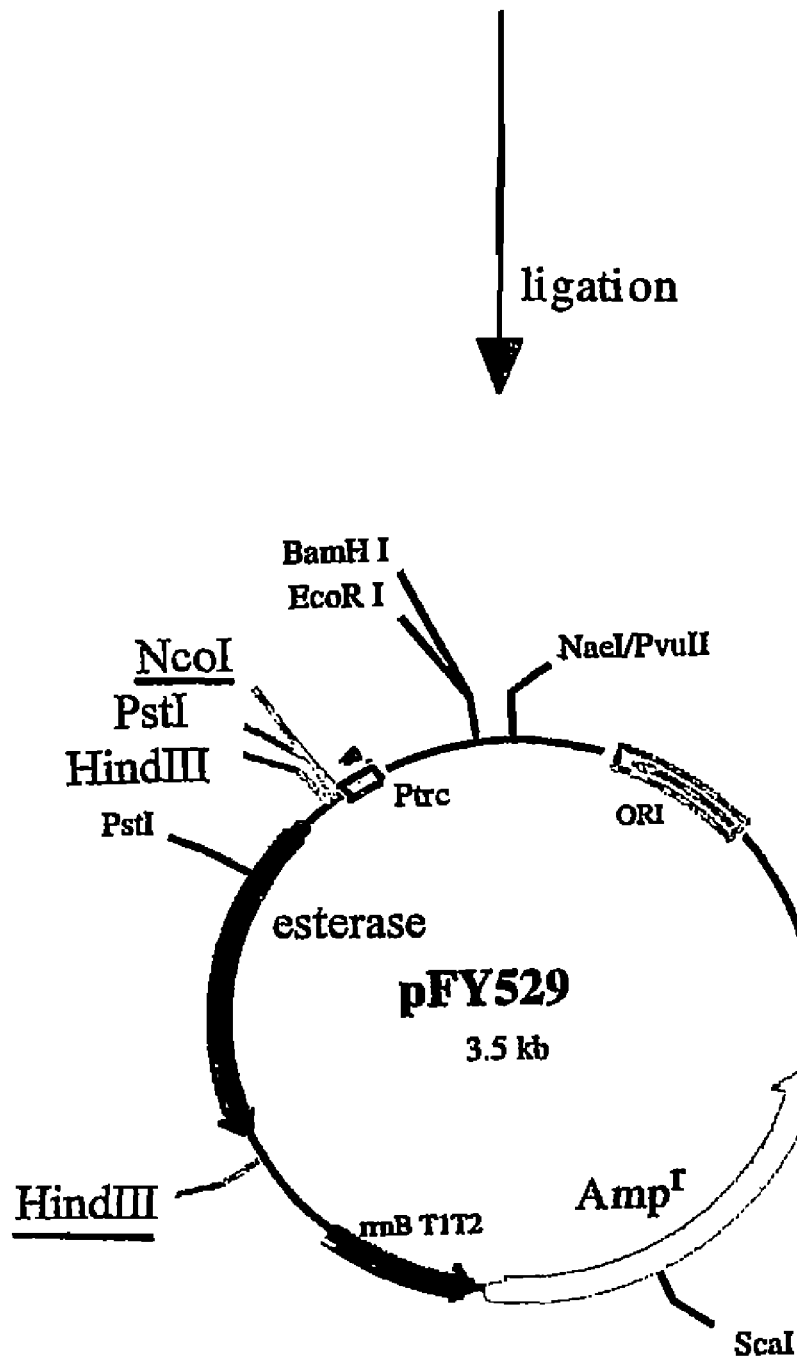

The plasmid pFY529 comprises an esterase gene derived from *Pseudomonas fluorescens*. The present plasmid was produced from the plasmid pFY520 described in Japanese Patent Application Laid-Open No. 1-67190 (FIGS. 5A and 5B). The plasmid pFY520 was deposited as a transformant "JM109/pFY520" with International Patent Organism Depositary, National Institute of Advanced Industrial Science and Technology, Independent Administrative Institution (at Tsukuba Central 6, 1-1-1 Higashi, Tsukuba, Ibaraki, Japan) under accession No. FERM BP-1469 (original deposition date: Sep. 3, 1987).

pFY520 was cleaved with the restriction enzyme NaeI, and ligation was then carried out using a HindIII linker to obtain a plasmid wherein the NaeI site of pFY520 was substituted with a HindIII site. This plasmid was named as pCF001. Such pCF001 was cleaved with the restriction enzyme HindIII to prepare an approximately 0.8 kb DNA fragment comprising an esterase gene. This fragment was inserted into the HindIII site of an expression vector pKK233-2, such that it is located in the same direction as that of a trc promoter, thereby obtaining a plasmid pCF002. Such pCF002 was cleaved with the restriction enzymes NaeI and ScaI, and the obtained fragment with a size of approximately 1.96 kb was ligated to an approximately 1.55 kb fragment obtained by cleaving a plasmid pUC18 with the restriction enzymes PvuII and ScaI to obtain a plasmid pFY529. Such pFY529 is equivalent to pCF002 (pKK233-2 vector) in that it has a trc promoter, but this plasmid is characterized in that it has a higher copy number.

INDUSTRIAL APPLICABILITY

The present invention provides an improved nitrile hydratase. The nitrile hydratase of the present invention is useful for efficiently producing an amide compound because it has high heat resistance and high substrate specificity.

| Sequence Listing | Free Text |
| --- | --- |
| SEQ ID NO: 5 | Synthetic DNA |
| SEQ ID NO: 6 | Synthetic DNA |
| SEQ ID NO: 7 | Synthetic DNA |
| SEQ ID NO: 8 | Synthetic DNA |
| SEQ ID NO: 9 | Synthetic DNA |
| SEQ ID NO: 10 | Synthetic DNA |
| SEQ ID NO: 11 | Synthetic DNA |
| SEQ ID NO: 11 | n is a, c, g, or t (existing at positions 20-21). |
| SEQ ID NO: 12 | Synthetic DNA |
| SEQ ID NO: 12 | n is a, c, g, or t (existing at positions 21-22). |
| SEQ ID NO: 13 | Synthetic DNA |
| SEQ ID NO: 14 | Synthetic DNA |
| SEQ ID NO: 14 | n is a, c, g, or t (existing at positions 21-22). |
| SEQ ID NO: 15 | Synthetic DNA |
| SEQ ID NO: 16 | Synthetic DNA |
| SEQ ID NO: 18 | Synthetic DNA |
| SEQ ID NO: 19 | Synthetic DNA |
| SEQ ID NO: 20 | Synthetic DNA |
| SEQ ID NO: 21 | Synthetic DNA |
| SEQ ID NO: 22 | Synthetic DNA |
| SEQ ID NO: 23 | Synthetic DNA |
| SEQ ID NO: 24 | Synthetic DNA |
| SEQ ID NO: 25 | Synthetic DNA |
| SEQ ID NO: 26 | Synthetic DNA |
| SEQ ID NO: 27 | Synthetic DNA |
| SEQ ID NO: 28 | Synthetic DNA |
| SEQ ID NO: 29 | Synthetic DNA |
| SEQ ID NO: 30 | Synthetic DNA |

The invention claimed is:

1. An isolated nucleic acid, which encodes a protein described in the following (a) or (b):
   (a) a protein, which comprises an amino acid sequence wherein at least one amino acid residue selected from among the phenylalanine residue at position 24, the isoleucine residue at position 88, the glutamic acid residue at position 92, the glutamic acid residue at position 93, the histidine residue at position 96, the glutamic acid residue at position 103, the asparagine residue at position 167, and the tyrosine residue at position 225, is substituted with another amino acid residue in the amino acid sequence of SEQ ID NO: 2 of the β subunit of a wild-type nitrile hydratase, and which has a heat-resistant nitrile hydratase activity; or
   (b) a protein, which comprises an amino acid sequence wherein the asparagine residue at position 167 is substituted with another amino acid sequence in the amino acid sequence of SEQ ID NO: 2 of the β subunit of a wild-type nitrile hydratase, and which has a heat-resistant nitrile hydratase activity.

2. An isolated nucleic acid described in the following (a) or (b):
   (a) an isolated nucleic acid, which comprises a nucleotide sequence wherein at least one nucleotide selected from among the nucleotides at positions 70 to 72, 262 to 264, 274 to 276, 277 to 279, 286 to 288, 307 to 309, 499 to 501, and 673 to 675, is substituted with another different nucleotide in the nucleotide sequence of SEQ ID NO: 1 of a nucleic acid encoding the β subunit of a wild-type nitrile hydratase, and which encodes a protein having a heat-resistant nitrile hydratase activity; or (b) an isolated nucleic acid, which comprises a nucleotide sequence wherein at least one nucleotide selected from among the nucleotides at positions 499 to 501 is substituted with another different nucleotide in the nucleotide sequence of SEQ ID NO: 1 of a nucleic acid encoding the β subunit of a wild-type nitrile hydratase, and which encodes a protein having a heat-resistant nitrile hydratase activity.

3. An isolated nucleic acid,
which comprises a nucleotide sequence wherein at least one nucleotide selected from among the nucleotides at positions 124 to 126, 238 to 240, 352 to 354, and 394 to 396, is substituted with another different nucleotide in the nucleotide sequence of SEQ ID NO: 3 of a nucleic acid encoding the α subunit of a wild-type nitrile hydratase, and which encodes a protein having a heat-resistant nitrile hydratase activity.

4. An isolated nucleic acid described in the following (a) or (b):
(a) an isolated nucleic acid, which comprises a nucleotide sequence wherein at least one nucleotide selected from among the nucleotides at positions 430 to 432 and 655 to 657 is substituted with another different nucleotide in a nucleotide sequence of SEQ ID NO: 1 wherein at least one nucleotide selected from among the nucleotides at positions 499 to 501 is substituted with another different nucleotide in the nucleotide sequence of SEQ ID NO: 1 of a nucleic acid encoding the β subunit of a wild-type nitrile hydratase, and which encodes a protein having a heat-resistant nitrile hydratase activity; or
(b) an isolated nucleic acid, which comprises a nucleotide sequence wherein with another different nucleotide at least one nucleotide selected from among the nucleotides at positions 499 to 501 in the nucleotide sequence of SEQ ID NO: 1 of a nucleic acid encoding the β subunit of a wild-type nitrile hydratase and the nucleotides at positions 385 to 387 and 586 to 588 in the nucleotide sequence of SEQ ID NO: 3 of a nucleic acid encoding the α subunit of a wild-type nitrile hydratase is substituted, and which encodes a protein having a heat-resistant nitrile hydratase activity.

5. An isolated nucleic acid,
which comprises a nucleotide sequence wherein at least one nucleotide selected from among the nucleotides at positions 76 to 78 and 142 to 144 is substituted with another different nucleotide in the nucleotide sequence of SEQ ID NO: 1 of a nucleic acid encoding the β subunit of a wild-type nitrile hydratase, and which encodes a protein having a heat-resistant nitrile hydratase activity.

6. The isolated nucleic acid according to claim 5, wherein base A at position 77 has been substituted with G.

7. The isolated nucleic acid according to claim 5, wherein base T at position 142 has been substituted with C.

8. A recombinant vector, which comprises the isolated nucleic acid according to any one of claims 1 to 7.

9. A transformant or transductant, which comprises the recombinant vector according to claim 8.

10. A method for producing a nitrile hydratase, which comprises culturing the transformant or transductant according to claim 9 and collecting a nitrile hydratase from a obtained culture.

11. An isolated nucleic acid, which encodes a protein,
which comprises an amino acid sequence wherein at least one amino acid residue selected from among the asparagine residue at position 42, the alanine residue at position 80, the alanine residue at position 118, and the asparatic acid residue at position 132, is substituted with another amino acid residue in the amino acid sequence of SEQ ID NO: 4 of the α subunit of a wild-type nitrile hydratase, and which has a heat-resistant nitrile hydratase activity.

12. An isolated nucleic acid, which encodes a protein described in the following (a) or (b):
(a) a protein, which comprises an amino acid sequence wherein the leucine residue at position 144 or the valine residue at position 219 is substituted with another amino acid residue, in an amino acid sequence wherein the asparagine residue at position 167 is substituted with another amino acid residue in the amino acid sequence of SEQ ID NO: 2 of the β subunit of a wild-type nitrile hydratase, and which has a heat-resistant nitrile hydratase activity; or
(b) a protein, which comprises an amino acid sequence wherein the asparagine residue at position 167 is substituted with another amino acid sequence in the amino acid sequence of SEQ ID NO: 2 of the β subunit of a wild-type nitrile hydratase and an amino acid sequence wherein the valine residue at position 129 or the leucine residue at position 196 is substituted with another amino acid residue in the amino acid sequence of SEQ ID NO: 4 of the a subunit of a wild-type nitrile hydratase, and which has a heat-resistant nitrile hydratase activity.

13. An isolated nucleic acid, which encodes a protein,
which comprises an amino acid sequence wherein at least one amino acid residue selected from the histidine residue at position 26 and the tryptophan residue at position 48 is substituted with another amino acid residue in the amino acid sequence of SEQ ID NO: 2 of the β subunit of a wildtype nitrile hydratase, and which has a heat-resistant nitrile hydratase activity.

14. The isolated nucleic acid of claim 13, wherein the histidine residue at position 26 of the encoded protein has been substituted with an arginine residue.

15. The isolated nucleic acid of claim 13, wherein the tryptophan residue at position 48 of the encoded protein has been substituted with any amino acid residue selected from among arginine, valine, and leucine.

* * * * *